(12) United States Patent
Brodkin et al.

(10) Patent No.: US 10,004,668 B2
(45) Date of Patent: Jun. 26, 2018

(54) NANOCRYSTALLINE ZIRCONIA AND METHODS OF PROCESSING THEREOF

(71) Applicant: Ivoclar Vivadent, Inc., Amherst, NY (US)

(72) Inventors: Dmitri G. Brodkin, Livingston, NJ (US); Yijun Wang, Basking Ridge, NJ (US); Ling Tang, Berkeley Heights, NJ (US); Ajmal Khan, Princeton, NJ (US); Anna B. Verano, Hillsborough, NJ (US)

(73) Assignee: Ivoclar Vivadent, Inc., Amherst, NY (US)

( * ) Notice: Subject to any disclaimer, the term of this patent is extended or adjusted under 35 U.S.C. 154(b) by 66 days.

(21) Appl. No.: 14/891,756

(22) PCT Filed: Jun. 12, 2014

(86) PCT No.: PCT/US2014/042140
§ 371 (c)(1),
(2) Date: Nov. 17, 2015

(87) PCT Pub. No.: WO2014/209626
PCT Pub. Date: Dec. 31, 2014

(65) Prior Publication Data
US 2016/0095798 A1    Apr. 7, 2016

Related U.S. Application Data

(60) Provisional application No. 61/840,055, filed on Jun. 27, 2013.

(51) Int. Cl.
*C04B 35/48* (2006.01)
*A61K 6/02* (2006.01)
(Continued)

(52) U.S. Cl.
CPC ............... *A61K 6/024* (2013.01); *A61C 5/70* (2017.02); *A61C 7/08* (2013.01); *A61C 8/0012* (2013.01);
(Continued)

(58) Field of Classification Search
CPC ..... C04B 35/48; C04B 35/482; C04B 35/484; C04B 35/486
See application file for complete search history.

(56) References Cited

U.S. PATENT DOCUMENTS 2,467,089 A    4/1949    Marisic et al.
4,758,541 A    7/1988    Tsukuma
(Continued)

FOREIGN PATENT DOCUMENTS

CA    2304166 A1    4/1999
CA    2383181 A1    11/2002
(Continued)

OTHER PUBLICATIONS

Kim et al. Effect of the number of coloring liquid applications on the optical properties of monolithic zirconia. Dental Materials 3 0 ( 2 0 1 4 ) e229-e237.*
(Continued)

*Primary Examiner* — Noah S Wiese
(74) *Attorney, Agent, or Firm* — Ann M. Knab; Thad McMurray

(57) ABSTRACT

Zirconia dental ceramics exhibiting opalescence and having a grain size in the range of 10 nm to 300 nm, a density of at least 99.5% of theoretical density, a visible light transmittance at or higher than 45% at 560 nm, and a strength of at least 800 MPa.

29 Claims, 16 Drawing Sheets

(51) Int. Cl.
*A61K 6/00* (2006.01)
*A61C 7/08* (2006.01)
*A61C 8/00* (2006.01)
*A61C 13/00* (2006.01)
*A61C 13/083* (2006.01)
*A61C 5/70* (2017.01)

(52) U.S. Cl.
CPC ............ *A61C 13/00* (2013.01); *A61C 13/083* (2013.01); *A61K 6/0008* (2013.01); *A61K 6/025* (2013.01)

(56) References Cited

U.S. PATENT DOCUMENTS

| | | | |
|---|---|---|---|
| 4,963,264 A | 10/1990 | Davis | |
| 5,553,630 A | 9/1996 | Dupuis | |
| 6,232,367 B1 | 5/2001 | Kobashigawa et al. | |
| 6,376,590 B2 | 4/2002 | Kolb et al. | |
| 6,787,080 B1 | 9/2004 | Lange et al. | |
| 6,869,501 B2 | 3/2005 | Davidson et al. | |
| 7,241,437 B2 * | 7/2007 | Davidson ............... | B82Y 30/00 423/593.1 |
| 7,429,422 B2 | 9/2008 | Davidson et al. | |
| 7,538,055 B2 | 5/2009 | Tsukuma et al. | |
| 7,655,586 B1 | 2/2010 | Brodkin et al. | |
| 7,674,523 B2 | 3/2010 | Davidson et al. | |
| 7,806,694 B2 | 10/2010 | Brodkin et al. | |
| 7,833,621 B2 | 11/2010 | Jones et al. | |
| 7,989,504 B2 | 8/2011 | Adam et al. | |
| 8,216,439 B2 | 7/2012 | Olevsky et al. | |
| 8,298,329 B2 | 10/2012 | Knapp et al. | |
| 8,309,015 B2 * | 11/2012 | Rolf ..................... | A61C 8/0012 264/16 |
| 8,425,809 B2 | 4/2013 | Ketharam et al. | |
| 8,598,058 B2 * | 12/2013 | Mathers ................. | B82Y 30/00 106/35 |
| 8,722,759 B2 | 5/2014 | Craig | |
| 9,120,200 B2 | 9/2015 | Haerle et al. | |
| 9,592,105 B2 | 3/2017 | Hauptmann et al. | |
| 9,657,152 B2 | 5/2017 | Kolb et al. | |
| 9,820,917 B1 | 11/2017 | Xu et al. | |
| 9,822,039 B1 | 11/2017 | Xu et al. | |
| 2004/0222098 A1 | 11/2004 | Clasen et al. | |
| 2006/0099552 A1 | 5/2006 | Van Der Zel et al. | |
| 2007/0273331 A1 | 11/2007 | Cross et al. | |
| 2008/0242746 A1 | 10/2008 | Morimura | |
| 2009/0004098 A1 | 1/2009 | Schmidt et al. | |
| 2009/0074655 A1 | 3/2009 | Suciu | |
| 2009/0115084 A1 | 5/2009 | Moon | |
| 2009/0189115 A1 | 7/2009 | Suciu | |
| 2009/0208746 A1 | 8/2009 | Suciu | |
| 2009/0274993 A1 | 11/2009 | Bergstrom et al. | |
| 2009/0294357 A1 | 12/2009 | Binner et al. | |
| 2010/0003630 A1 | 1/2010 | Yamashita et al. | |
| 2010/0075170 A1 | 3/2010 | Adair et al. | |
| 2010/0254149 A1 | 10/2010 | Gill | |
| 2011/0027742 A1 | 2/2011 | Fujisaki et al. | |
| 2011/0064977 A1 | 3/2011 | Wendel et al. | |
| 2011/0230340 A1 | 9/2011 | Binner et al. | |
| 2012/0058883 A1 | 3/2012 | Yamashita et al. | |
| 2012/0264588 A1 | 10/2012 | Kolb | |
| 2012/0277088 A1 | 11/2012 | Mathers et al. | |
| 2013/0313738 A1 | 11/2013 | Carden | |
| 2014/0147387 A1 | 5/2014 | Butts et al. | |
| 2015/0238291 A1 | 8/2015 | Hauptmann et al. | |
| 2015/0328813 A1 | 11/2015 | Shi Liyi et al. | |
| 2016/0095798 A1 | 4/2016 | Brodkin et al. | |

FOREIGN PATENT DOCUMENTS

| | | |
|---|---|---|
| JP | 2002200100 A | 7/2002 |
| JP | 2002236312 A | 8/2002 |
| JP | 3100119 U | 4/2004 |
| JP | 2004230122 A | 8/2004 |
| JP | 2008061469 A | 3/2008 |
| JP | 2010011668 A | 1/2010 |

OTHER PUBLICATIONS

Adam, J., et al. "Milling of Zirconia Nanoparticles in a Stirred Media Mill," J. Am. Ceram. Soc., 91 [9] 2836-2843 (2008).
Alaniz, J. E., et al. "Optical Properties of Transparent Nanocrystalline Yttria Stabilized Zirconia," Opt. Mater., 32, 62-68 (2009).
Anselmi-Tamburini, et al., "Transparent Nanometric Cubic and Tetragonal Zirconia Obtained by High-Pressure Pulsed Electric Current Sintering," Adv. Funct. Mater. 17, 3267-3273 (2007).
Apetz, R., et al., "Transparent Alumina: A Light Scattering Model," J. Am. Ceram. Soc., 86 [3], 480-786 (2003).
Binner, J., et al., "Processing of Bulk Nanostructured Ceramics," J. Eur. Ceram. Soc. 28, 1329-1339 (2008).
Binner, J., et al., "Compositional Effects in Nanostructured Yttria Partially Stabilized Zirconia," Int. J. Appl. Ceram. Tec., 8, 766-782 (2011).
Casolco, S.R. et al, "Transparent/translucent polycrystalline nanostructured yttria stabilized zirconia with varying colors," Scripta Mater. 58 [6], 516-519 (2007).
Garcia, et al., "Structural, Electronic, and Optical Properties of ZrO2 from Ab Initio Calculations," J. Appl. Phys., 100 [1], 104103 (2006).
Klimke, et al., Transparent Tetragonal Yttria-Stabilized Zirconia Ceramics, J. Am. Ceram. Soc., 94 [6] 1850-1858 (2011).
Knapp, K., "Understanding Zirconia Crown Esthetics and Optical Properties," Inclusive Magazine, (2011).
Rignanese, et al., "First-principles Study of the Dynamical and Dielectric Properties of Tetragonal Zirconia," Phys. Rev. B, 64 [13], 134301 (2001).
Srdic, V. V., et al. "Sintering Behavior of Nanocrystalline Zirconia Prepared by Chemical Vapor Synthesis," J. Am. Ceram. Soc. 83 [4], 729-736 (2000).
Srdic, V.V., et al., "Sintering Behavior of Nanocrystalline Zirconia Doped with Alumina Prepared by Chemical Vapor Synthesis," J. Am. Ceram. Soc. 83 [8], 1853-1860 (2000).
Trunec, et al., "Compaction and Presureless Sintering of Zirconia Nanoparticles," J. Am. Ceram. Soc. 90 [9] 2735-2740 (2007).
Cho, M.-S. et al., "Opalescence of all-ceramic core and veneer materials," Dental Materials, 25, 695-702 (2009).
Egen, M., et al., "Artificial Opals as Effect Pigments in Clear-Coatings," Macromol. Mater. Eng. 289, 158-163 (2004).
Lee, Y.-K., et al., "Measurement of Opalescence of Resin Composites," Dental Materials 21, 1068-1074 (2005).
Lee, Y.-K., et al., "Changes in Opalescence and Fluorescence Properties of Resin Composites after Accelerated Aging," Dental Materials 22, 653-660 (2006).
Lee, Y.-K, "Influence of Scattering/Absorption Characteristics on the Color of Resin Composites," Dental Materials 23, 124-131 (2007).
Lee, Y.-K, "Measurement of Opalescence of Tooth Enamel," Journal of Dentistry 35, 690-694 (2007).
White, et al., "Biological Organization of Hydroxyapatite Crystallites into a Fibrous Continuum Toughens and Controls Anisotropy in Human Enamel," J.Dent. Res. 80(1): 321-326, (2001).
Peelen, J. G. J. et al., "Light Scattering by Pores in Polycrystalline Materials: Transmission Properties of Alumina," Journal of Applied Physics, 45, 216-220 (1974).
Primus, C. M., et al., "Opalescence of Dental Porcelain Enamels," Quintessence International, 33, 439-449 (2002).
Yu, B., et al., "Difference in Opalescence of Restorative Materials by the Illuminant," Dental Materials 25, 1014-1021 (2009).
Dialysis, Obtained from https://www.merriam-webster.com/dictionary/dialysis on Oct. 10, 2017.
Schwartz et al., "Introduction to Tangential Flow Filtration for Laboratory and Process Development Applications," Obtained from http://www.pall.com/main/laboratory/literature-library-details.page?id=34212 on Oct. 10, 2017.

* cited by examiner

Figure 3
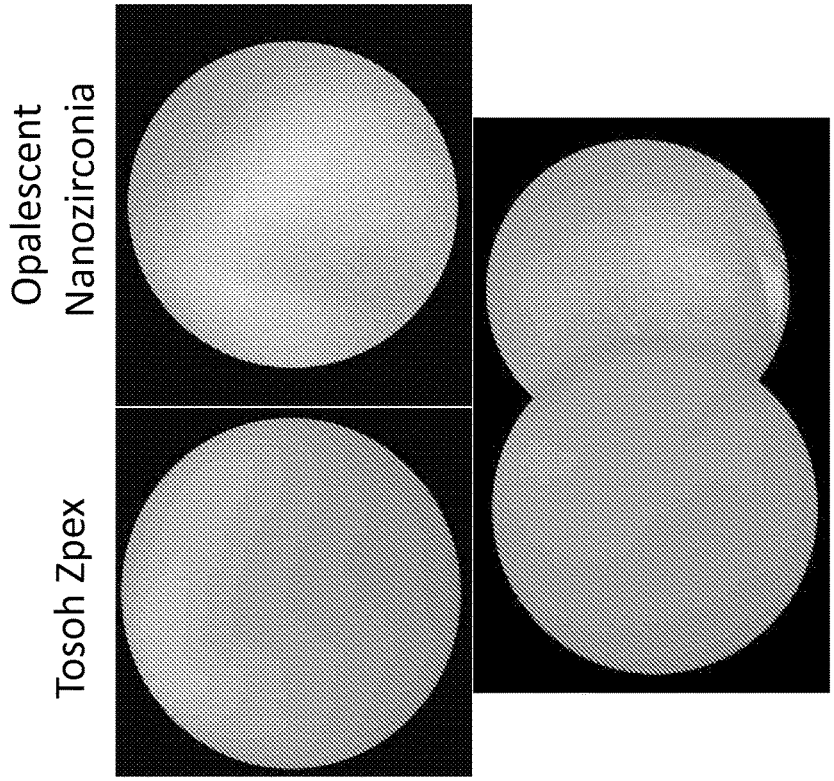
Figure 3B
Figure 3A

NANOCRYSTALLINE ZIRCONIA AND METHODS OF PROCESSING THEREOF

CROSS-REFERENCE TO RELATED APPLICATIONS

This application is a National Stage application of International Patent Application No. PCT/US2014/042140 filed on Jun. 12, 2014, which claims priority to U.S. Application No. 61/840,055, filed Jun. 27, 2013, entitled Nanocrystalline Zirconia And Methods Of Processing Thereof, the disclosures of which are incorporated herein by reference in their entirety.

TECHNICAL FIELD

The present invention is directed to dental restorations comprising nanozirconia and methods of processing thereof, and more particularly to nanozirconia dental ceramics combining translucency that matches glass-ceramics, opalescence mimicking natural dentition and high strength characteristic of tetragonal zirconia.

BACKGROUND

Currently, the best commercially available full contour (monolithic) zirconia dental ceramic materials are aesthetically inferior to lithium disilicate or leucite-based glass ceramic materials like IPS e.max or IPS Empress due to lower translucency and lack of opalescence. Better light transmittance and opalescence are required to better mimic natural dentition. Human enamel has varying "anisotropic" translucency which introduces many optical effects that are difficult to replicate with ceramic material. Opalescence is one optical characteristic of natural enamel that can create a highly complex visual display. To date, only glass ceramic materials come close to duplicating such optical complexity of natural dentition including opalescence. At the same time glass-ceramic materials are not as strong as zirconia materials hence limiting their clinical use to single- and multi-unit restorations and cases without bruxism.

U.S. Pat. No. 8,309,015, which is hereby incorporated by reference in its entirety, is directed to a method of processing tetragonal nanozirconia with grain sizes under 100 nm. The sintered body is claimed to only contain pores smaller than about 25 nm. The method is lacking bulk shape consolidation technology and does not address, mention or discuss opalescence. Rather, the requirements set forth in the patent and claims include the diameter of any pores which are present in the translucent zirconia sintered body to be not more than about 25 nm, which as believed, would preclude this material from being in the desired opalescent range as taught in the present invention and also is unrealistic for any practical bulk shape consolidation technology yielding dental articles via pressureless sintering.

U.S. Pat. No. 8,598,058, which is hereby incorporated by reference in its entirety, is directed to a method of processing nanozirconia articles with grain sizes under 200 nm and pore size under 50 nm comprising from about 0.5% to about 5.0% lanthanum oxide claimed to be essential to achieve the claimed properties. Again this patent does not address, mention or discuss opalescence despite showing sintered bodies illuminated with incident light whereby opalescence would be obvious if present.

U.S. Pat. No. 7,655,586 and No. 7,806,694, both hereby incorporated by reference in their entirety, are directed to a dental article and fabrication methods comprising: a single component yttria-stabilized tetragonal zirconia ceramic material having grains of average grain size exceeding 100 nanometers and not exceeding about 400 nanometers, wherein the ceramic material is fabricated of particulate material consisting essentially of ceramic crystallites with an average size of less than about 20 nm; wherein the particulate material is sintered without application of external pressure at a temperature less than about 1300° C. to a full density wherein the final pore size does not exceed the size of the ceramic crystallite size; and wherein the ceramic material exhibits at least 30% relative transmission of visible light when measured through a thickness of about 0.3 to about 0.5 mm Again the requirements set forth in the patents and claims limit the diameter of pores and achievable grain size distributions which are present in the translucent zirconia sintered body, which as believed would preclude this material from being opalescent.

The following patents and published applications, directed to zirconia ceramics or processing methods, are hereby incorporated by reference in their entirety: U.S. Pat. No. 6,787,080, U.S. Pat. No. 7,655,586, U.S. Pat. No. 7,806,694 U.S. Pat. No. 7,833,621, U.S. Pat. No. 7,674,523, U.S. Pat. No. 7,429,422, U.S. Pat. No. 7,241,437, U.S. Pat. No. 6,376,590, U.S. Pat. No. 6,869,501, U.S. Pat. No. 8,298,329, U.S. Pat. No. 7,989,504, U.S. Pat. No. 8,425,809, U.S. Pat. No. 8,216,439, U.S. Pat. No. 8,309,015, U.S. Pat. No. 7,538,055, U.S. Pat. No. 4,758,541, US20110027742, US20120058883, US20100003630, US20090274993, US20090294357, US20090115084, US20110230340, US20090004098, US20100075170, US20040222098, and US20130313738. Among them U.S. Pat. No. 8,298,329 and US20130313738 describe translucent nano-crystalline dental ceramics and a process of fabrication of the same by slip-casting or powder compaction.

The following publications are directed to processing and properties of zirconia or transparent alumina ceramics.

Adam, J., et al. "Milling of Zirconia Nanoparticles in a Stirred Media Mill", J. Am. Ceram. Soc., 91 [9] 2836-2843 (2008)

Alaniz, J. E., et al. "Optical Properties of Transparent Nanocrystalline Yttria Stabilized Zirconia", Opt. Mater., 32, 62-68 (2009)

Anselmi-Tamburini, etc al. "Transparent Nanometric Cubic and Tetragonal Zirconia Obtained by High-Pressure Pulsed Electric Current Sintering", Adv. Funct. Mater. 17, 3267-3273 (2007)

Apetz, R., et al. "Transparent Alumina: A Light Scattering Model", J. Am. Ceram. Soc., 86 [3], 480-486 (2003)

Binner, J., et al. "Processing of Bulk Nanostructured Ceramics", J. Eur. Ceram. Soc. 28, 1329-1339 (2008)

Binner, J. et al. "Compositional Effects in Nanostructured Yttria Partially Stabilized Zirconia" Int. J. Appl. Ceram. Tec., 8, 766-782 (2011)

Casolco, S. R. et al. "Transparent/translucent polycrystalline nanostructured yttria stabilized zirconia with varying colors" Scripta Mater. 58 [6], 516-519 (2007)

Garcia, et al. "Structural, Electronic, and Optical Properties of $ZrO_2$ from Ab Initio Calculations", J. Appl. Phys., 100 [1], 104103 (2006)

Klimke, et al. "Transparent Tetragonal Yttria-Stabilized Zirconia Ceramics" J. Am. Ceram. Soc., 94 [6] 1850-1858 (2011)

Knapp, K. "Understanding Zirconia Crown Esthetics and Optical Properties", Inclusive Magazine, (2011)

Rignanese, et al, "First-principles Study of the Dynamical and Dielectric Properties of Tetragonal Zirconia" Phys. Rev. B, 64 [13], 134301 (2001)

Srdic, V. V., et al. "Sintering Behavior of Nanocrystalline Zirconia Prepared by Chemical Vapor Synthesis" J. Am. Ceram. Soc. 83 [4], 729-736 (2000)

Srdic, V. V., et al. "Sintering Behavior of Nanocrystalline Zirconia Doped with Alumina Prepared by Chemical Vapor Synthesis" J. Am. Ceram. Soc. 83 [8], 1853-1860 (2000)

Trunec, et al. "Compaction and Presureless Sintering of Zirconia Nanoparticles" J. Am. Ceram. Soc. 90 [9] 2735-2740 (2007)

Vladimir V. Srdic', Markus Winterer, and Horst Hahn. "Sintering Behavior of Nanocrystalline Zirconia Prepared by Chemical Vapor Synthesis". J. Am. Ceram. Soc., 83 [4] 729-36 (2000)

Most or all of the above-listed patents and publications describe a variety of properties of tetragonal nanozirconia materials and processing methods thereof. All of these sources appear to describe sintering with application of external pressure such as HIP or SPS.

Light transmission at about 550-560 nm is commonly accepted to compare light transmittance of dental materials, especially dental zirconia materials, which is related to the color resolution/sensitivity of photopic vision of human eyes. In humans, photopic vision allows color perception, mediated by cone cells in the retina. The human eye uses three types of cones to sense light in three bands of color. The biological pigments of the cones have maximum absorption values at wavelengths of about 420 nm (bluish-violet), 534 nm (Bluish-Green), and 564 nm (Yellowish-Green). Their sensitivity ranges overlap to provide vision throughout the visible spectrum from about 400 nm to about 700 nm. Colors are perceived when the cones are stimulated, and the color perceived depends on how much each type of cone is stimulated. The eye is most sensitive to green light (555 nm) because green stimulates two of the three kinds of cones almost equally; hence light transmission at 560 nm is used as a basis for characterization of highly translucent zirconia materials of the present invention.

Opalescence is one of the important optical characteristics of natural dentition that is critical to replicate in aesthetic dental restorative material in order to fabricate life-like dental restorations. This esthetic requirement is often referred to as the "vitality of a restoration". It is a well-known optical effect resulting in a bluish appearance in reflected color and an orange/brown appearance in transmitted color. The opalescent property is generally associated with scattering of the shorter wavelengths of the visible spectrum, by inclusions of the second phase(s) having a different refractive index from the matrix phase. In human teeth, opalescence of natural enamel is related to light scattering and dispersion produced by complex spatial organization of enamel's elemental constituents—hydroxyapatite nanocrystals. Hydroxyapatite crystallites forming human enamel are arranged in bundles or sheets forming rods (bundles) and interrods (sheets), which are organized in a honeycomb-like structure. The average crystal size is 160 nm long and 20-40 nm wide. As light travels through the enamel, the rods scatter and transmit the shorter wavelength light, rendering the enamel opalescent.

The degree of opalescence can be quantified by a colorimetric spectrophotometry measurement with a CIE standard. For example, Lee et al. (see references below) use "Opalescence Parameter" (OP) as a measure of opalescence. Kobashigawa et. al. (U.S. Pat. No. 6,232,367) use the same basic formula, but termed it "Chromaticity Difference". The opalescence parameter (OP or "Chromaticity Difference") is calculated according to the following formula: OP= $[(CIEa_{T*}-CIEa_{R*})^2+(CIEb_{T*}-CIEb_{R*})^2]^{1/2}$, wherein $(CIEa_{T*}-CIEa_{R*})$ is the difference between transmission and reflectance modes in red-green coordinate a*; $(CIEb_{T*}-CIEb_{R*})$ is the difference between transmission and reflectance modes in yellow-blue color coordinate b*. Using this formula, OP of the commercially available current state of the art "translucent" zirconia is calculated to be in the range from about 5 to about 7. These commercial materials are clearly not opalescent. According to literature data, it is believed that materials with low OP values are not opalescent. The measured OP range for clearly opalescent human enamel was 19.8-27.6. According to Kobashigawa, for matching the vitality of natural teeth, the OP value should be at least 9, and preferably higher, so that the opalescence effect is clearly observed. On the other hand it is not useful to match high OP values of human enamel "just by numbers" since the restoration will not blend well with the adjacent teeth in the patient's mouth.

The following publications are directed to mechanisms of opalescence in natural or synthetic materials.

Cho, M.-S. et al. "Opalescence of all-ceramic core and veneer materials", Dental Materials, 25, 695-702, (2009)

Egen, M. et al. "Artificial Opals as Effect Pigments in Clear-Coatings", Macromol. Mater. Eng. 289, 158-163, (2004)

Lee, Y.-K., et al. "Measurement of Opalescence of Resin Composites", Dental Materials 21, 1068-1074, (2005)

Lee, Y.-K., et al. "Changes in Opalescence and Fluorescence Properties of Resin Composites after Accelerated Aging", Dental Materials 22, 653-660, (2006)

Lee, Y.-K., "Influence of Scattering/Absorption Characteristics on the Color of Resin Composites" Dental Materials 23, 124-131, (2007)

Lee, Y.-K., "Measurement of Opalescence of Tooth Enamel", Journal of Dentistry 35, 690-694, (2007)

Kobashigawa, A. I. et al., "Opalescent Fillers for Dental Restorative Composites", U.S. Pat. No. 6,232,367 B1, (2001)

Peelen. J. G. J. et al. "Light Scattering by Pores in Polycrystalline Materials: Transmission Properties of Alumina", Journal of Applied Physics, 45, 216-220, (1974)

Primus, C. M., et al. "Opalescence of Dental Porcelain Enamels" Quintessence International, 33, 439-449, (2002)

Yu, B., et al. "Difference in Opalescence of Restorative Materials by the Illuminant", Dental Materials 25, 1014-1021, (2009)

White et al., Biological Organization of Hydroxyapatite Crystallites into a Fibrous Continuum Toughens and Controls Anisotropy in Human Enamel, J Dent Res 80(1): 321-326, (2001).

It would be extremely beneficial to have high translucency of glass ceramics combined with high strength of tetragonal zirconia and opalescence mimicking natural dentition in the same dental restorative material sinterable below 1200° C., which can be processed into a full contour zirconia restoration using conventional techniques and equipment such as dental CAD/CAM systems, dental pressing furnaces and dental furnaces. Other techniques and equipment successfully used in other areas of technology for mass production of near-net shaped parts and components can be also used.

SUMMARY

These and other features are achieved by nanozirconia bodies of the present invention. In one embodiment, certain ranges of processing conditions are utilized to produce nanozirconia bodies that are opalescent in green, brown (pre-sintered) and fully dense condition as shown in FIG. 2. Opalescent nanozirconia bodies can be also nearly transparent or highly translucent in all stages of processing (visible light transmittance at or higher than 45% and preferably higher than 50% at 560 nm for 1 mm samples) and result in fully dense tetragonal zirconia bodies (at least 99.5% or higher density and preferably ≥99.9% dense) that in addition to high light transmittance also comprise high strength (at least 800 MPa or higher strength and preferably ≥1200 MPa strength) and sinterability at temperatures below 1200° C. in conventional dental furnaces which is especially important for dental restorative applications.

FIG. 1 shows the spectral (wavelength) dependence of light transmittance within visible light range of 400-700 nm for a variety of dental materials including the current state of the art commercial "translucent" zirconia brands fabricated from Zpex™ and Zpex™ Smile powders made by Tosoh (Japan). Light transmittance of Zpex™ and Zpex™ Smile made materials measured at 560 nm, the wavelength of visible light of aforementioned "maximal physiological significance," is 39% and 46%, respectfully for 1 mm samples. The difference in light transmittance between Zpex™ and Zpex™ Smile samples is related to their Yttria ($Y_2O_3$) content and resulting phase composition: while Zpex™-made zirconia comprising 3 mole % of $Y_2O_3$ is tetragonal, Zpex Smile made zirconia (~5.3 mole % of $Y_2O_3$) is comprising both tetragonal and cubic phases, hence it is more translucent but only half as strong as tetragonal zirconia (~1200 MPa vs ~600 MPa, respectfully). Both materials as well as other commercial zirconia materials are clearly not opalescent.

By comparing curves presented in FIG. 1 it becomes apparent that opalescent nanozirconia materials of the present invention have steeper spectral transmittance curves as measured in transmittance mode by a conventional visible light spectrophotometer equipped with an integrating sphere. This is consistent with the fact that being opalescent, nanozirconia materials of the present invention scatter blue light, i.e. shorter wavelengths, preferentially, while allowing yellowish red light, i.e. longer wavelengths, to transmit through with limited scattering. Thus, it allows us to define their advantageous light transmittance properties as being higher than 45% and preferably higher than 50% in the whole spectral range of 560 nm to 700 nm for unshaded or "naturally colored" nanozirconia and higher than 35% and preferably higher than 40% in the whole spectral range of 560 nm to 700 nm for shaded nanozirconia intentionally doped with coloring ions such as Fe, Cr, Ni, Co, Er, Mn and other ions/oxides listed in U.S. Pat. Nos. 6,713,421 and 8,178,012 which are hereby incorporated by reference in their entirety. Typically, light transmittance of shaded zirconia is 5-10% lower than light transmittance of unshaded or "naturally colored" zirconia.

In tetragonal nanozirconia of the present invention, it is believed that opalescence comes from the interaction of visible light with the specific crystal structure and grain/pore size distributions. In particular, we speculate that scattering mainly occurs due to the existence of residual pores and/or grain size dependent birefringence and the associated differences in refractive index between pores and tetragonal zirconia matrix or between different crystallographic orientations in a crystal lattice of individual nanozirconia crystallites. In this complex optical phenomenon or combination of optical phenomena resulting in opalescence, both total porosity and pore size distribution will affect the pore related scattering in all stages of nanozirconia processing from green to brown to sintered bodies; while contribution of birefringence intrinsic to tetragonal zirconia is dependent on the grain size distribution in partially or fully sintered bodies. Normally the pore and grain sizes in well-formed nanozirconia compacts are of the same scale and increasing concurrently with densification and grain growth. The desired level of opalescence exists only for specific combination of porosity, and pore/grain size distributions. Selective scattering of only the short wavelengths of visible light is the key to achieve a combination of optical opalescence and a high level of translucence. It can be speculated that one of the applicable scattering models is Rayleigh scattering, in which the size of scattering species are much smaller than the incident wavelength, the intensity of scattering (I) is strongly dependent on wavelength, and the scattered intensity on both forward and backward directions are equal for a specific wavelength. According to Rayleigh scattering theory, the fact that scattering cross-section $\sigma_s$ is proportional to $\lambda^{-4}$, where $\lambda$ is the wavelength of the incident light explains why the shorter (blue) wavelengths are scattered more strongly than longer (red) wavelengths. For example, the same nanoscale scattering center/site would scatter a wavelength at 430 nm (in the blue range) by a factor of 6 times more efficiently compared to a wavelength of 680 nm (in the red range). As a result, an observer will find that the samples appear bluish in color when observing from the same side of the light source while yellowish and reddish when observing from the opposite side of the light source. This unique characteristic of nanozirconia materials of the present invention occurs only for specific processing methods and starting materials described below resulting in such specific grain and pore size distributions during a transition from a transparent to a translucent stage within the overall grain size range of 10 nm to 300 nm and final pore size mostly larger than 25 nm, and preferably larger than 30 nm with total porosity being less than 0.5% and preferably less than 0.1% (in the fully dense nanozirconia bodies). The average grain size in translucent opalescent zirconia of the present invention as measured according to ASTM E112-12 test method is from 40 nm to 150 nm, preferably from 50 to 100 nm, and most preferably from 50 to 80 nm.

The materials of the present invention are especially useful for full contour restorations combining the strength of zirconia with aesthetics of glass-ceramics benchmarks.

In various embodiments, dental restorations comprising opalescent nanozirconia can be shaped by milling, injection molding, electrophoretic deposition, gel-casting etc.

Opalescent nanozirconia dental restorations of the present invention comprise the following key features:

Opalescent with OP values above 9 and preferably above 12.

Nearly transparent or highly translucent in shaded or unshaded (natural) condition: Light transmittance of at least 45% and preferably higher than 50% at a wavelength of 560 nm or even in the whole spectral range of 560 nm to 700 nm for unshaded or "naturally colored" nanozirconia for 1 mm samples; and higher than 35% and preferably higher than 40% at 560 nm or even in the whole spectral range of 560 nm to 700 nm for shaded nanozirconia intentionally doped with coloring ions for 1 mm samples.

Predominantly tetragonal, i.e., major phase is tetragonal zirconia (less than 10% cubic) and preferably YTZP, i.e., Yttria Stabilized Tetragonal Zirconia Polycrystal with $Y_2O_3$ content within the range from 0 to 3 mole %.

Grain size within overall range from 10 nm to 300 nm, or 20 nm to 250 nm, in fully sintered condition as confirmed by analysis of fracture surfaces (see representative fracture surface in FIGS. 11A, 11B and 11C).

The average grain size in translucent opalescent zirconia of the present invention as measured according to ASTM E112 (or EN 623-3) test method is from 40 nm to 150 nm, preferably from 50 to 100 nm, and most preferably from 50 to 80 nm.

Pore size mostly larger than 25 nm, preferably 30 nm when density is higher than 99.5%. Most preferably that porosity is less than 0.1% (density ≥99.9% of theoretical density) for maximal visible light transmittance.

Strong—ISO 6872 flexural strength at least 800 MPa or higher, and preferably ≥1200 MPa strength; and most preferably ≥2 GPa strength.

Sinterable at temperatures<1200° C. using conventional dental furnaces or microwave dental furnaces.

Shaped by CAD/CAM, EPD, LPIM, dental heat-pressing (like glass ceramic ingots) similar to LPIM and gel-casting using RP molds.

The zirconia may include a stabilizing additive selected from Y, Ce, Mg, or mixtures thereof, or other known stabilizing additive.

The numbers and ranges in the specification and claims can cover values obtained by applying the regular rules of rounding and/or up to +/−5%.

BRIEF DESCRIPTION OF THE DRAWINGS

Embodiments of the present invention will be more fully understood and appreciated by the following Detailed Description in conjunction with the accompanying drawings, in which:

FIGS. 3A and 3B compare light transmittance and opalescence of the nanozirconia materials of the present invention in green, brown and fully dense condition to commercial dental zirconia materials in a fully dense condition.

DETAILED DESCRIPTION

Figure 1:
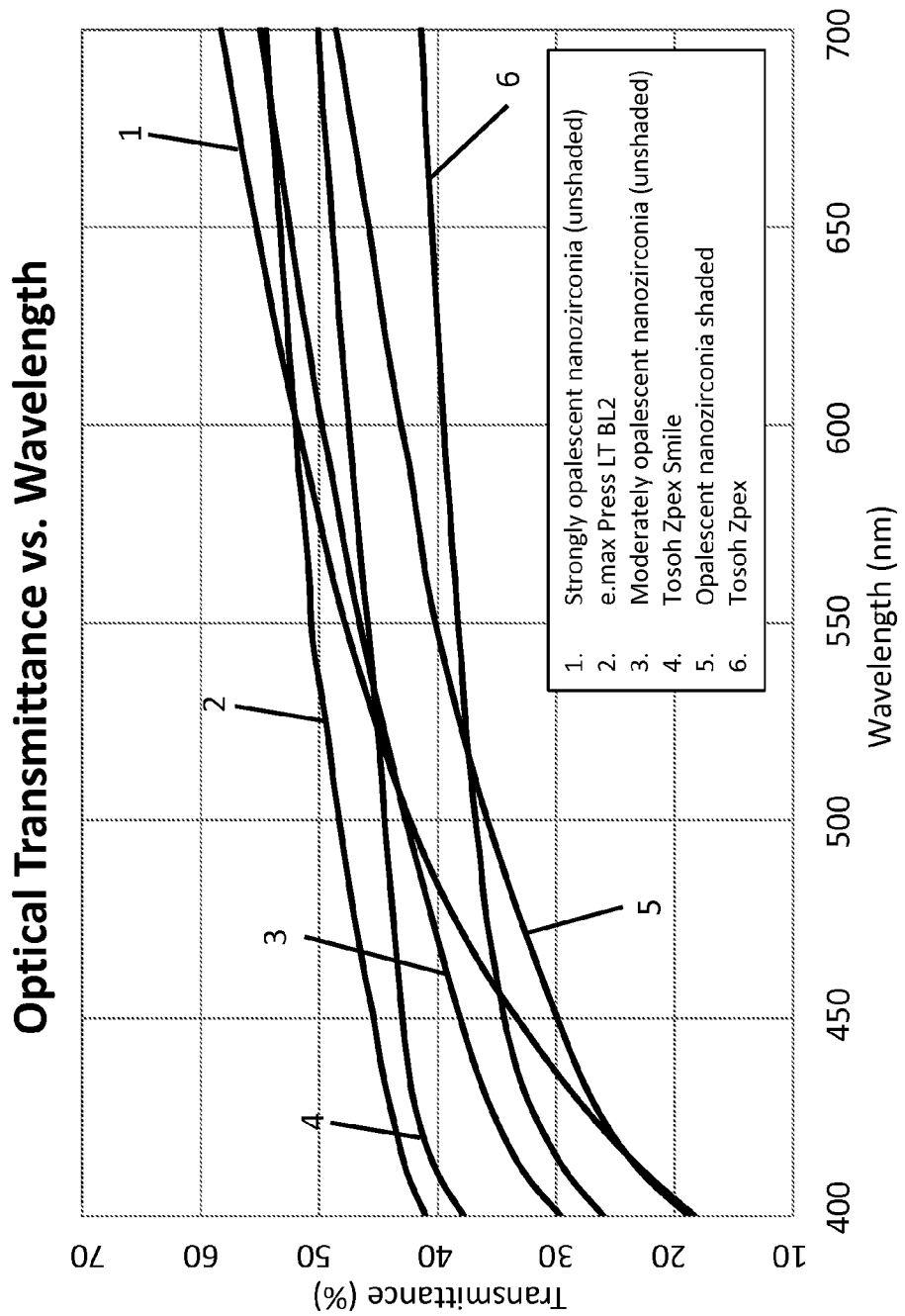
FIG. 1 shows the spectral (wavelength) dependence of light transmittance within visible light range of 400-700 nm for a variety of dental materials including the current state of the art commercial "translucent" zirconia brands fabricated from Zpex™ and Zpex™ Smile powders made by Tosoh (Japan).
Figure 2:
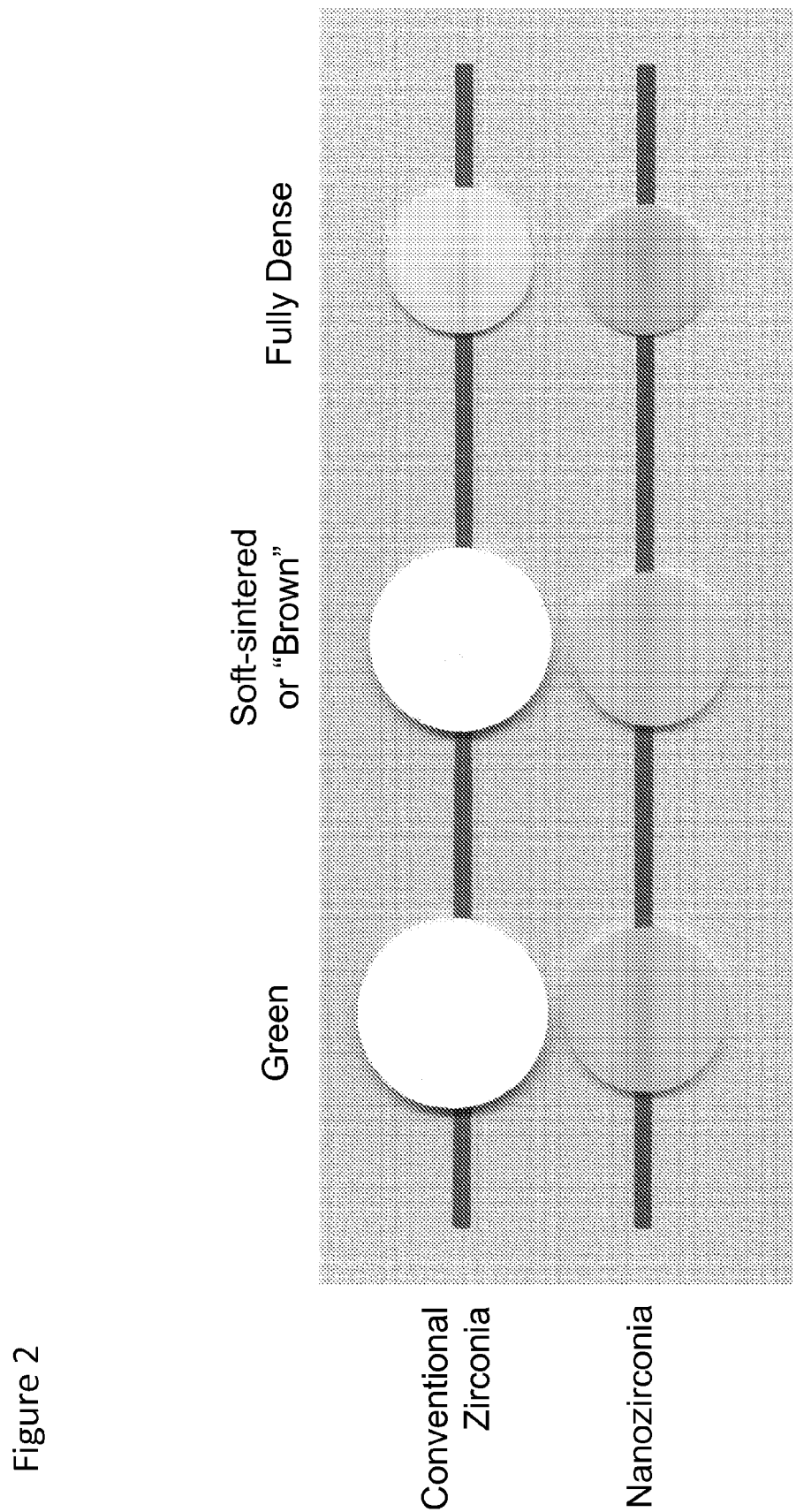
FIG. 2 shows transition of tetragonal nanozirconia material of this invention from nearly transparent green to translucent fully dense stage.

It was surprisingly found that within a certain range of processing conditions and starting particle sizes the resulting nanozirconia bodies are opalescent in green, brown (or pre-sintered) and, most importantly, in fully dense condition. Opalescent nanozirconia bodies can be also nearly transparent or highly translucent in all stages of the processing and result in fully dense bodies (at ≥99.5% dense) that in addition to high light transmittance also comprise high strength (≥800 MPa and even in excess of 2 GPa) and sinterable at temperatures below 1200° C. in conventional dental furnaces which is especially important for dental restorative applications. The materials of the present invention are especially useful for full contour restorations combining strength of zirconia with aesthetics of glass-ceramics benchmarks. Dental restorations comprising opalescent nanozirconia can be shaped by machining/milling, injection molding, dental heat-pressing, electrophoretic deposition, gel-casting and other dental technologies or technologies used in industry at large for shaping high-performance ceramics. Specifically, CAD/CAM blanks can be formed by slip-casting (coarser nanoparticulates only), centrifugal casting, drop-casting, injection molding, filter-pressing and electrophoretic deposition (EPD).

It is specific pore size distribution and/or grain size distribution that are believed to render predominantly single phase tetragonal zirconia of this invention both highly translucent and opalescent. We can speculate that in order to generate opalescence in a fully dense nanozirconia, at least a portion, preferably a major portion of scattering species (e.g. tetragonal grains with anisotropic refractive index and occasional nano-pores) form some kind of "optical sub-lattice" and have a characteristic size or diameter within a specific, fairly narrow range. Within this range the scattering species are large enough to cause adequate scattering of blue light yet small enough to not cause much scattering of yellow-red light, which can be explained by the Rayleigh scattering model. Rayleigh approximation is generally applicable to scattering species much less than wavelength of light or specifically for birefringence effects when tetragonal grain size is at least an order of magnitude less than wavelength of visible light. Mie model is not restricted by grain size. Both models coincide when the grain size is less than 50 nm. Maximized opalescence will be achieved when present scattering species are about or just below the sizes transitional between the Rayleigh and the Mie models (where they start to diverge). It can be further speculated that once their size exceeds the transitional range, the opalescence effect will largely disappear as the less wavelength-dependent Mie scattering mechanism is operational. This upper size limit for opalescence is dictated by differences in refractive index between the pores and the tetragonal zirconia matrix and/or between different crystallographic orientations in a crystal lattice of individual nanozirconia crystallites. In addition, another critical factor that imposes an upper limit on the size of scattering species (mostly grains since residual porosity is minimal) is high translucence required for aesthetic dental ceramics. Also shading of nanozirconia invariably further lowers overall visible light transmittance imposing further constraints on grain size distribution to achieve the same light transmittance. Typically light transmittance of shaded zirconia is about 5-10% lower than light transmittance of unshaded or "naturally colored" zirconia.

Opalescence and other physical properties of the materials of the present invention can be quantified within the following ranges:

To further illustrate the advantageous properties listed in the table above, FIGS. 3A and 3B compare light transmittance and opalescence of the nanozirconia materials of the present invention to commercial dental zirconia materials. In one preferred embodiment, the process schematically shown in FIG. 4 will result in green or pre-sintered (brown) millable blanks that can be further processed into dental articles such as dental restorations (blanks, full-contour FPDs (fixed partial dentures), bridges, implant bridges, multi-unit frameworks, abutments, crowns, partial crowns, veneers, inlays, onlays, orthodontic retainers, space maintainers, tooth replacement appliances, splints, dentures, posts, teeth, jackets, facings, facets, implants, cylinders, and connectors) using commercially available dental CAD/CAM systems. In the alternative embodiments, dental articles can be formed directly from suspension by EPD, gel-casting in the enlarged molds formed by rapid-prototyping (RP). In another alternative embodiment, nanoparticulates of the present invention can be provided as feed-stock for injection molding. In the latter case the enlarged molds for low-pressure injection molding (LPIM) can be formed

| Property | Broad Range | Preferred Range |
|---|---|---|
| Phase composition and chemistry | Predominantly tetragonal zirconia with less than 15% monoclinic and cubic phase combined. | YTZP (yttria-stabilized tetragonal zirconia polycrystal) with 0-3 mol % $Y_2O_3$ |
| Opalescence | Visually opalescent with OP values above 9 | OP values preferably above 12 |
| Nearly transparent or highly translucent in shaded or unshaded (natural) condition | Light transmittance higher than 45% at wavelength of 560 nm or even in the whole spectral range of 560 nm to 700 nm for unshaded or "naturally colored" nanozirconia; and higher than 35% at 560 nm or even in the whole spectral range of 560 nm to 700 nm for shaded nanozirconia intentionally doped with coloring ions (to match internal or external shade standards approximating tooth colors) | Preferably light transmittance higher than 50% at wavelength of 560 nm or even in the whole spectral range of 560 nm to 700 nm for unshaded or "naturally colored" nanozirconia; and higher than 40% at 560 nm or even in the whole spectral range of 560 nm to 700 nm for shaded nanozirconia intentionally doped with coloring ions (to match internal or external shade standards approximating tooth colors). |
| Overall grain size range in fully sintered condition | At least 95% of grains by volume are from 10 nm to 300 nm in size (or diameter), or 20 nm to 250 nm in size (diameter) | All grains are from 10 nm to 300 nm in size (or diameter) |
| Average grain size measured according to ASTM E112 (or EN 623-3) test method | From 40 nm to 150 nm, | Preferably from 50 to 100 nm, and most preferably from 50 to 80 nm. |
| Density/residual porosity in fully sintered condition | Pore size mostly larger than 30 nm wherein density is higher than 99.5%. | Most preferably that porosity is less than 0.1% (density ≥99.9% of theoretical density) |
| Flexural strength | ISO 6872 flexural strength at least 800 MPa or higher | Preferably ≥1200 MPa flexural strength; and most preferably ≥2 GPa flexural strength |
| Sinterable at temperatures <1200° C. without application of external pressure (pressureless sintering) | Sinterable at temperatures <1200° C. using conventional dental furnaces or microwave dental furnaces | Sinterable at temperatures ≤1150° C. using conventional dental furnaces or microwave dental furnaces |
| Shaped by CAD/CAM, EPD, LPIM, dental heat-pressing (like glass ceramic ingots) similar to LPIM and gel-casting using RP molds | Preferred way is machining of partially sintered blanks formed by slip-casting (limited use - for coarser nanoparticulates only), centrifugal casting, drop-casting, gel-casting, injection molding, filter-pressing and electrophoretic deposition (EPD) | | by RP. RP is useful to form molds that are enlarged to compensate for isotropic sintering shrinkage of the materials of the present invention when they are sintered from green or pre-sintered state to a full density.

Figure 4:
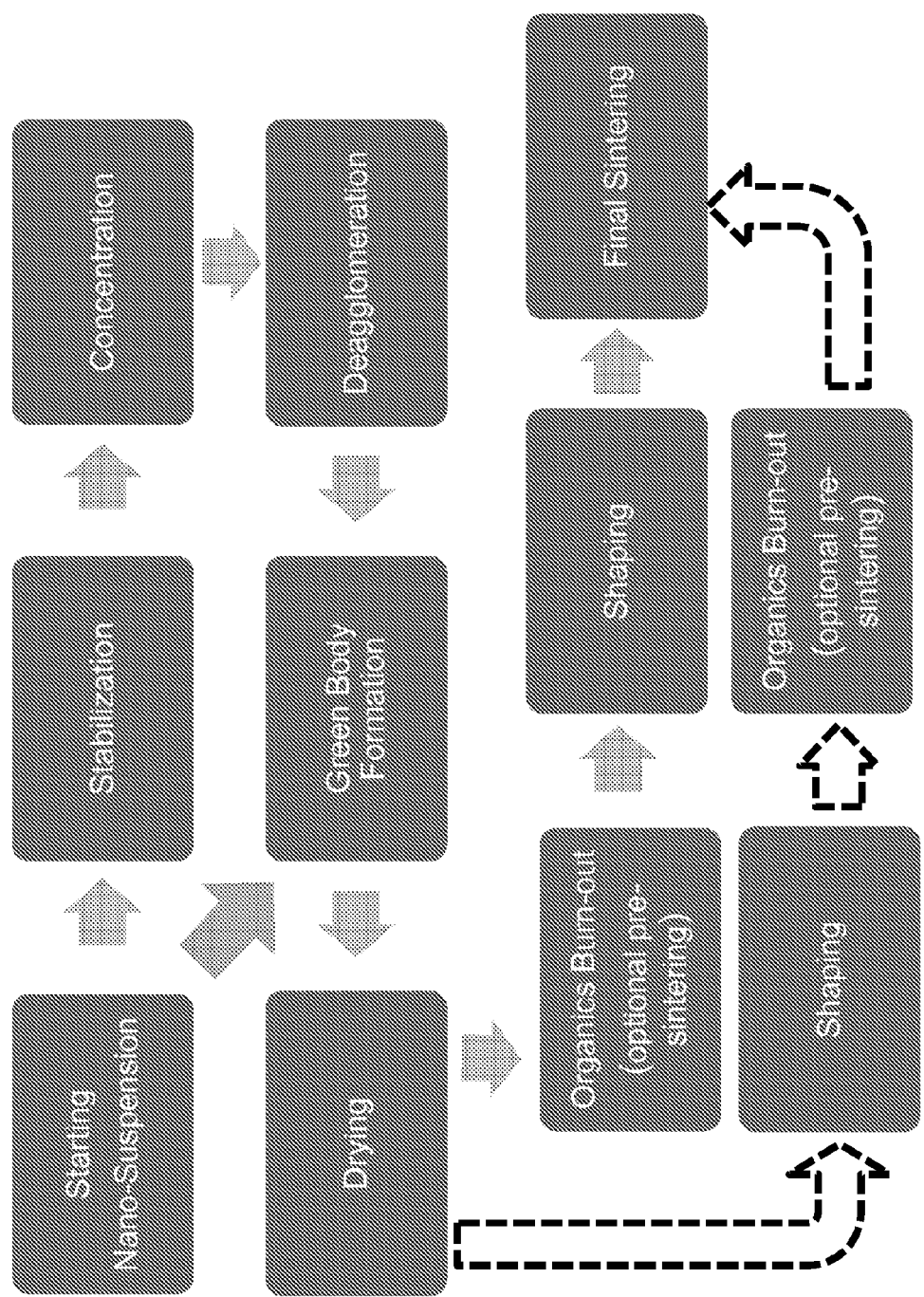
FIG. 4 shows a generic flowchart of the processing method of the present invention.
Figure 5:
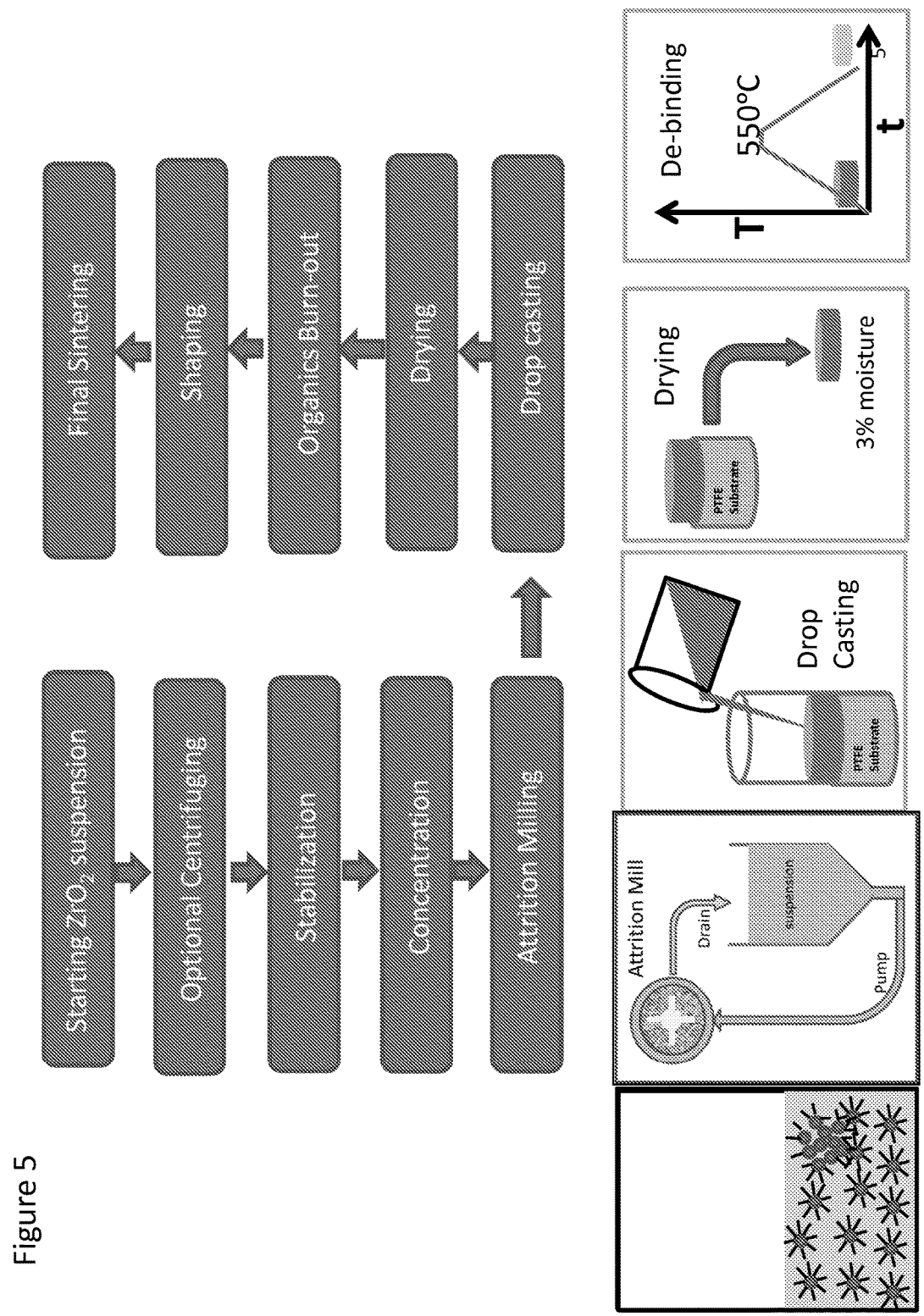
FIG. 5 shows a flowchart of an embodiment of the process in accordance with the present invention.

It is important to note that highly translucent tetragonal nanozirconia bodies were produced from two types of nanozirconia suspensions spanning the wide range of processing scenarios as shown in the flow chart in FIG. 4. Organic based Pixeligent (Pixeligent Technologies, Baltimore, Md.) nanozirconia suspensions (0% $Y_2O_3$) with solid loading of ~14 vol % and aqueous based MEL (MEL Chemicals, Flemington, N.J.) suspension of 3Y-TZP (3 mole % $Y_2O_3$) with solid loading of ~5 vol %.

EXAMPLES

The non-limiting examples illustrating some of the embodiments and features of the present invention are further elucidated in FIGS. 6-13. Commercially available nanozirconia suspensions were received from various manufacturers. The most useful suspensions preferably comprise well-dispersed nanoparticles with average primary particle size of ≤20 nm and preferably ≤15 nm. In certain cases nanosuspensions comprising partially agglomerated and/or associated nanoparticles can be also used with average particulate size up to 40-80 nm. The latter will require attrition milling to deagglomerate and commune nanoparticles to the required size range. The starting zirconia concentration is usually low, e.g. 5 vol %, but concentrated suspensions are also available from some manufacturers (see FIG. 13B). These concentrated suspensions may contain proprietary dispersants. The liquid medium of the suspension is preferably water, and can also be organic solvents, e.g. ethanol, methanol, toluene, dimethylformamide, etc. or mixtures of such. The suspension was stabilized by addition of dispersants and adjustment of pH. A dispersant used to stabilize nanosuspensions in the examples below was one of the following: Poly(ethyleneimine), 2-[2-(2-Methoxyethoxy)ethoxy]acetic acid, or 2-(2-Methoxyethoxy)acetic acid. The amount of dispersants by weight of solid zirconia was no more than 10% (e.g., from 0.5 wt % up to 10 wt %). The pH values of suspension were in the range of 2 to 13. Centrifuging and/or attrition milling may be applied to remove and/or break the agglomerated/aggregated portion of solids prior to or after stabilizing the suspensions. In some cases, binders may be added to the suspension in order to enhance the strength of the cast. The suspensions were then concentrated by evaporating off the solvents at elevated temperature with or without vacuum assistance. After concentration, the suspension will be above 10 vol %, e.g. preferably at least 14 vol %, preferably 16%, most preferably 18 vol %, and up to 50 vol % depending on requirements of forming methods. After concentration, the viscosity (measured at 25° C.) of concentrated suspensions prior to casting was well below 100 cP and in most cases below 30 cP, most preferably viscosity should be at or below 15 cP as this level of viscosity produced best casting results. Attrition milling may also be used during or after the concentrating process primarily to break down agglomerates and aggregates and sometimes to reduce particle size.

The concentrated zirconia suspensions with desired solid loadings were then used to cast zirconia green bodies. The forming methods include: slip-casting, gel-casting, electrophoretic deposition, drop-casting, filter pressing, injection molding, and centrifugal casting as well as other known applicable forming methods. After casting, the green bodies were dried in a temperature, pressure, and humidity controlled environment to ensure forming crack-free articles. The drying conditions are usually dictated by the dimensions of the articles: e.g. thicker articles require longer drying time to prevent cracking. After drying, green bodies were at least 35%, preferably 45%, more preferably over 50% of theoretical density. Dried green bodies were burnt out to remove the organic species including dispersants, binders, and any other additives. The peak burn-out temperature was no higher than 700° C., preferably from 500° C. to 600° C. Optional pre-sintering can be carried out at temperatures up to 850° C. After burn out, the articles, so-called "brown" bodies, were then sintered at temperatures lower than 1200° C. to reach full density. Sintering can be carried out in dental furnaces, traditional high temperature furnaces, or hybrid microwave furnaces. Density of the sintered articles was measured by the Archimedes method using water as the immersion medium. Relative density, calculated using a theoretical density value of 6.08 g/cm³, is usually ≥99.5% in fully sintered articles in the current invention.

The fully sintered samples were then ground to 1.0 mm for optical property measurement. Transmittance and reflectance were measured by a Konica Minolta Spectrophotometer CM-3610d, according to the CIELAB color scale in the reflectance and transmittance mode relative to the standard illuminant D65. The aperture diameter was 11 mm for reflectance measurement, and 20 mm for transmittance measurement. Measurements were repeated five times for each specimen and the values were averaged to get the final reading. The transmittance of green bodies through 1 mm thickness was at least 50% at 560 nm, and was at least 45% for the brown bodies.

Opalescence parameter was calculated as:
$OP=[(CIEa_{T*}-CIEa_{R*})^2+(CIEb_{T*}-CIEb_{R*})^2]^{1/2}$, whereas $(CIEa_{T*}-CIEa_{R*})$ is the difference between transmission and reflectance modes in red-green coordinate, a* of CIE L*a*b* color space; $(CIEb_{T*}-CIEb_{R*})$ is the difference between transmission and reflectance modes in yellow-blue color coordinate, b* of CIE L*a*b* color space.

The biaxial flexural strength measurements were performed by an MTS Q Test machine on disk samples with a thickness of 1.2±0.2 mm according to ISO6872-2008. Sintered samples were also polished, thermally etched and imaged under Zeiss Sigma Field Emission scanning electron microscope (SEM). Average grain size was calculated by the intercept method according to ASTM E112-12.

Example 1

2 kg of 5 vol % aqueous suspension of yttria (3 mol %) stabilized zirconia nanoparticulate was received from Mel Chemicals (Flemington, N.J.). This suspension was de-agglomerated by centrifuging at 7000 rpm for 40 minutes. The suspension was then stabilized by adding 2% dispersants by weight of solid zirconia. The pH of such stabilized suspension was 2.5. This suspension was concentrated from 5 vol % to 18 vol % of solid loading with an Ika RV10 vacuum evaporator at 40° C. and 40 mbar for about 4 hours. Cylindrical PTFE molds of from 18 mm to 32 mm in diameter and 10 mm in height were prepared, and the zirconia suspension was poured into the molds. 5 to 15 g of slurry was applied to each mold depending on the desired final thickness. Then molds with suspension were put into an environmental chamber for curing and drying. For the first 72-120 hours, the humidity was above 85% and temperature was about 25° C. The drying time was determined by the thickness of the samples. The thicker samples took a longer time to dry without generating cracks. Then environmental humidity decreased gradually to about 20%, where final water content in the green bodies reached less than 4 wt %. The as-formed green bodies were ~49% of theoretical density. Transmittance was 58% for 2 mm thick green body at 560 nm. Dried green bodies were burned out by heating at a rate of 0.5° C./min to 550° C. and holding for 2 hours. The brown bodies, of 1.8 mm thick, had transmittance of 49% at 560 nm. The brown bodies were then sintered in a dental furnace (Programat P500, Ivoclar Vivadent AG.) at a ramp rate of 10° C./min to 1150° C., held for 2 hours, and then cooled naturally in air. After sintering, the disk samples were from 12 to 23 mm in diameter and 1.5 mm in thickness, with relative density of 99.98%. Probably due to contamination by Fe, Ni or Cr from the stainless steel equipment used in manufacturing of the starting nanozirconia suspensions, all fully sintered samples in Example 1 to Example 6 appeared tinted, i.e., noticeably yellow-brownish in color with a hue that resembles the natural tooth color.

Figure 7:
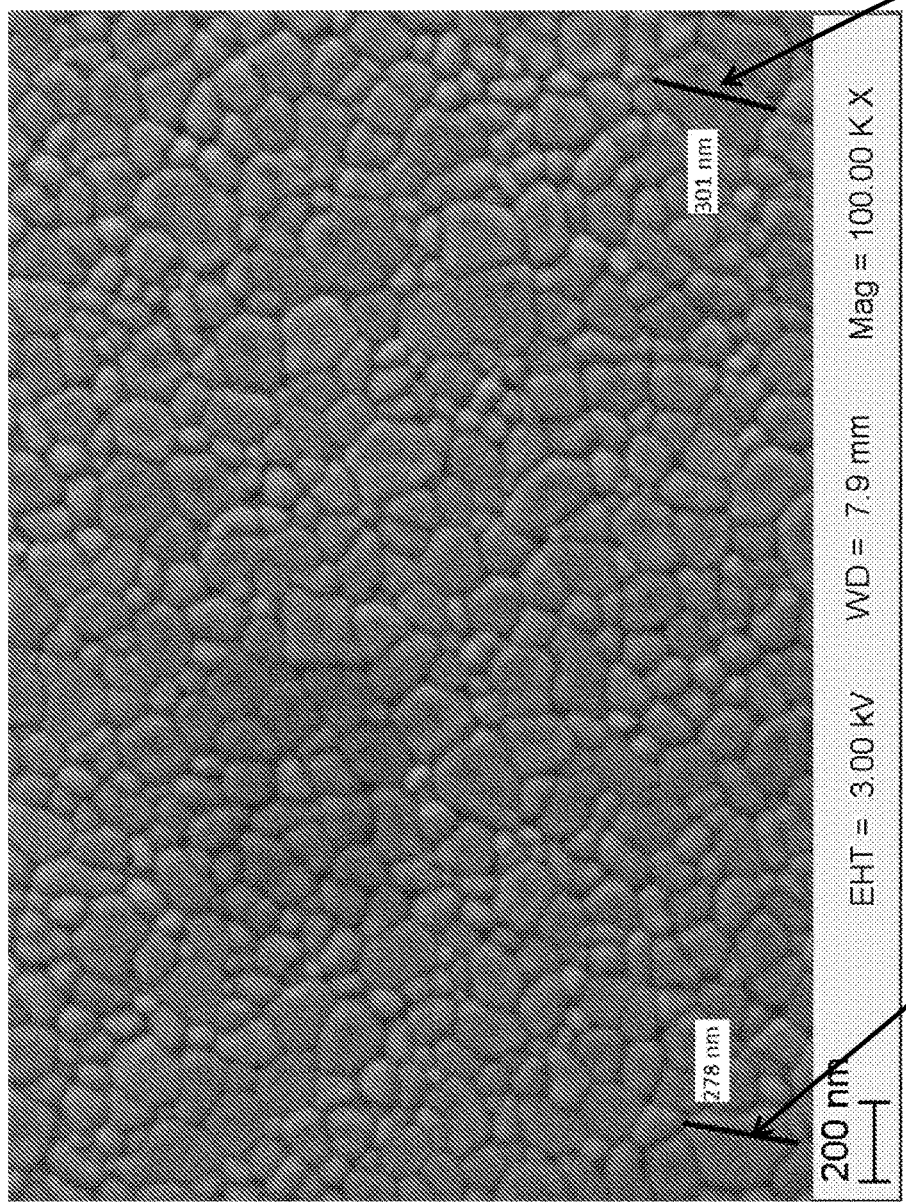
FIG. 7 shows a microstructure of 99.9% dense opalescent nanozirconia body with average grain size of 136 nm sintered in a conventional dental furnace in accordance with the present invention as described in Example 1A.

The samples were then ground down to thickness of 1.0 mm for transmittance and reflectance measurements. The transmittance of such "tinted" samples was 37.7%, and opalescence factor was 13.6. An SEM image of a polished and thermally etched cross-section is shown in FIG. 7, and the average grain size is 136 nm. The biaxial flexural strength is 2108±386 MPa.

In the following parallel experiments, all processing conditions remained identical, except that the binder burn out and/or sintering conditions were modified.

For Example 1B, sintering was carried out at 1125° C. for 2 hours.

In example 1C to 1F, a 2-step sintering method was adapted, by heating the samples to a higher temperature (e.g. 1125° C., 1150° C.) for very short time (e.g. 6 seconds), and then quickly dropping to lower temperature (e.g. 1075° C., 1050° C.) and holding for a prolonged period of time.

Figure 8:
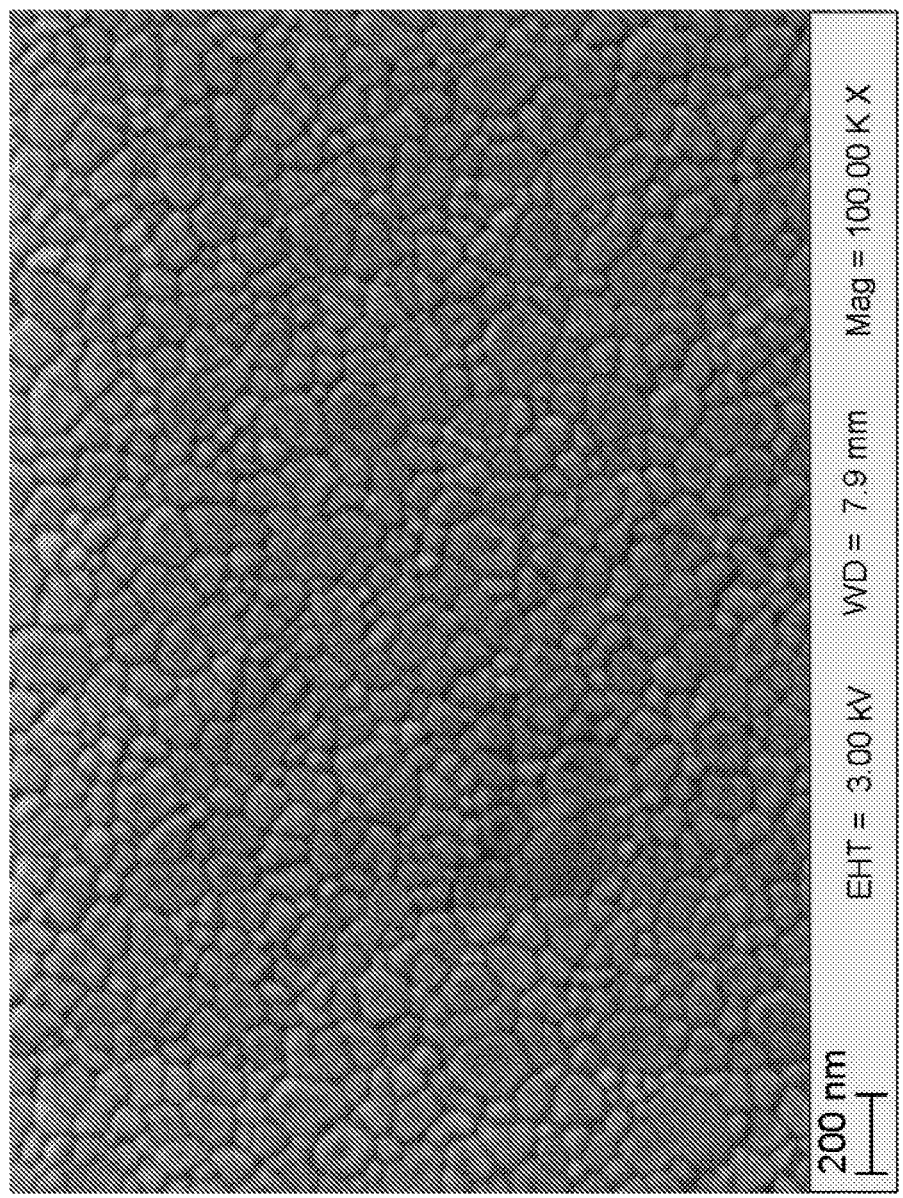
FIG. 8 shows a microstructure of 99.9% dense opalescent nanozirconia body with average grain size of 112 nm sintered in a conventional dental furnace in accordance with the present invention as described in Example 1C.

In Example 1C, the sample was heated from room temperature to 1125° C. at 10° C./min rate and held at 1125° C. for 6 seconds; then it was cooled down to 1075° C. quickly and held at 1075° C. for 20 hours. An SEM image of a polished and thermally etched cross-section is shown in FIG. 8, and the average grain size is 112 nm. Biaxial flexural strength is 1983±356 MPa.

In example 1D, the sample was heated from room temperature to 1150° C. at 10° C./min rate and held at 1150° C. for 6 seconds; then it was cooled down to 1075° C. quickly and held at 1075° C. for 20 hours. Biaxial flexural strength is 2087±454 MPa.

In example 1E, the sample was heated from room temperature to 1125° C. at 10° C./min rate and held at 1125° C. for 6 seconds; then it was cooled down to 1075° C. quickly and held at 1075° C. for 15 hours.

In example 1F, the sample was heated from room temperature to 1125° C. at 10° C./min rate and held at 1125° C. for 10 seconds; then it was cooled down to 1075° C. quickly and held at 1075° C. for 20 hours.

In another parallel experiment, the binder burn-out conditions were altered. Example 1G was processed at all identical conditions as Example 1C, except the peak burn out temperature was raised from 550° C. to 700° C.

Results on density, biaxial flexural strength, grain size, light transmittance, and opalescence measurements are summarized in Table 1 below.

TABLE 1

| Example | Dispersant | Solid Loading (vol %) | Sintering | Relative Density % | Biaxial Flexural Strength (MPa) | Average Grain size (nm) | Light Transmission @ 560 nm | Color | Opalescence Factor |
|---|---|---|---|---|---|---|---|---|---|
| 1A | 2% | 18 | 1150/2 h | 99.98 | 2108 ± 386 | 136 | 38 | yellow-brownish, tooth like hue | 14 |
| 1B | 2% | 18 | 1125/2 h | 99.96 | — | 114 | 38 | yellow-brownish, tooth like hue | 14 |
| 1C | 2% | 18 | 1125/6 s-1075/20 h | 99.95 | 1983 ± 356 | 112 | 40 | yellow-brownish, tooth like hue | 15 |
| 1D | 2% | 18 | 1150/6 s-1075/20 h | 99.90 | 2087 ± 454 | — | 39 | yellow-brownish, tooth like hue | — |
| 1E | 2% | 18 | 1125/6 s-1075/15 h | 99.91 | — | — | 39 | yellow-brownish, tooth like hue | 14 |
| 1F | 2% | 18 | 1125/10 s-1075/20 h | 99.92 | — | — | 38 | yellow-brownish, tooth like hue | 15 |
| 1G | 2% | 18 | 1125/6 s-1075/20 h | 99.92 | — | — | 39 | yellow-brownish, tooth like hue | 13 |
| 2A | 2% | 18 | 1100/4 h | 99.94 | — | 108 | — | yellow-brownish, tooth like hue | — |
| 2B | 2% | 18 | 1125/2 h | 99.94 | — | — | 38 | yellow-brownish, tooth like hue | — |
| 2C | 2% | 18 | 1100/3 h | 99.96 | — | — | 39 | yellow-brownish, tooth like hue | 14 |
| 2D | (2 + 3)% | 18 | 1125/2 h | 99.90 | — | — | — | yellow-brownish, tooth like hue | — |
| 2E | 4% | 18 | 1125/2 h | 99.92 | — | 119 | — | yellow-brownish, tooth like hue | — |
| 3A | 2% | 14 | 1150/2 h | 99.92 | — | 131 | 37 | yellow-brownish, tooth like hue | — |
| 3B | 2% | 14 | 1125/6 s-1075/20 h | 99.91 | — | 107 | 39 | yellow-brownish, tooth like hue | — |
| 4A | 2% | 18 | 1125 C./2 h | 99.86 | — | — | — | yellow-brownish, tooth like hue | — |
| 4B | 2% | 18 | 1125/6 s-1075/20 h | 99.92 | — | 91 | — | yellow-brownish, tooth like hue | — |
| 5 | 2% | 18 | 1150/2 h | 99.50 | — | — | — | yellow-brownish, tooth like hue | — |

TABLE 1-continued

| Example | Dispersant | Solid Loading (vol %) | Sintering | Relative Density % | Biaxial Flexural Strength (MPa) | Average Grain size (nm) | Light Transmission @ 560 nm | Color | Opalescence Factor |
|---|---|---|---|---|---|---|---|---|---|
| 6 | 2% | 18 | 1150/2 h | 99.90 | — | — | — | yellow-brownish, tooth like hue | — |

Example 2

The suspension preparation and concentration steps were identical to Example 1A. After concentration and prior to casting, an addition step, attrition milling, was carried out using Netzsch MiniCer attrition mill. The concentrated suspension was milled with 200, 100, or 50 µm of yttria stabilized zirconia beads at 3000 rpm rotation speed. After attrition milling, the suspension was cast into PTFE molds, dried, and burned out in the same procedures as in Example 1A.

For Example 2A, the attrition milling time was 1 hours, and the brown bodies were sintered at 1100° C. for 4 hours.

For Example 2B, the attrition milling time was 1.5 hours, and the brown bodies were sintered at 1125° C. for 2 hours.

For Example 2C, the attrition milling time was 1.5 hours, and the brown bodies were sintered at 1100° C. for 3 hours.

For Example 2D, after original attrition milling for 1.5 hours at 3000 rpm in the attrition mill, an additional 3 wt % (according to the weight of zirconia) of additives was added to the suspension. Attrition milling continued another 1 hour. The suspension was cast into molds, dried, and burned out in same procedures as in Example 1A. The sample was then sintered at 1125° C. for 2 hours.

For Example 2E, the suspension and preparation steps were identical to Example 1A except that 4 wt % of dispersant was used. After concentration, attrition milling was performed for 3 hours. The samples were sintered at 1125° C. for 2 hours.

Figure 9:
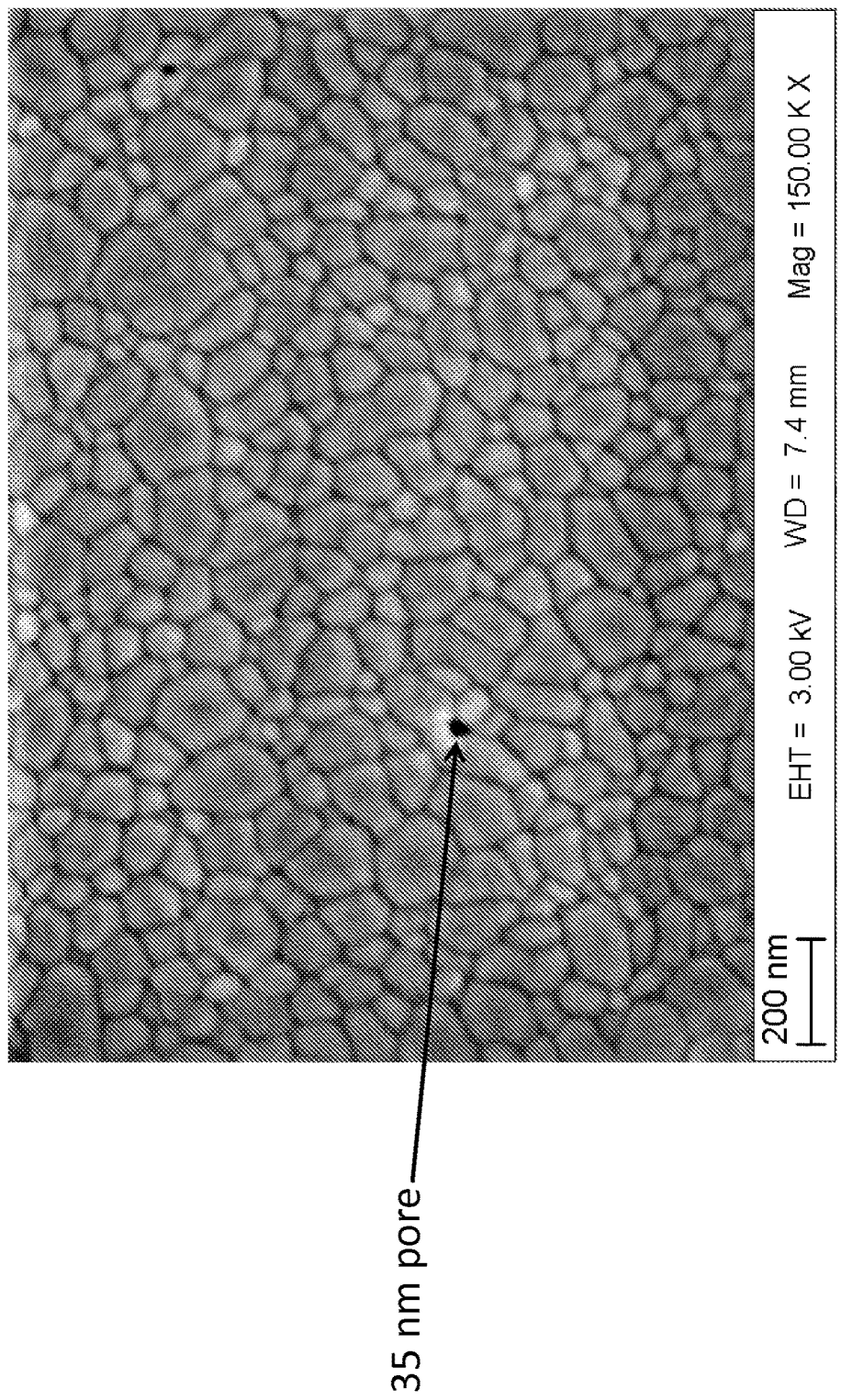
FIG. 9 shows a microstructure of 99.9% dense opalescent nanozirconia body with average grain size of 108 nm sintered in conventional dental furnace in accordance with the present invention as described in Example 2A with a pore of at least 35 nm marked in the SEM micrograph.

Density, optical properties, and grain size were measured and reported in Table 1. SEM image of Example 2A is shown in FIG. 9, where a ~35 nm diameter pore was observed. All samples are visually opalescent.

Example 3

In the stabilization step, a different dispersant of 2 wt % was used in comparison to Example 1A, and the suspension was concentrated to 14 vol %. After concentration, the suspension was cast into the molds. Drying and burning out were carried out at identical procedures as Example 1A.

For Example 3A, the sample was heated to 1150° C. at 10° C./min and held for 2 hours.

For Example 3B, the sample was heated to 1125° C. with 10° C./min rate and held at 1125° C. for 10 seconds; then it was cooled down to 1075° C. quickly and held at 1075° C. for 20 hours.

Density, optical properties, and grain size were measured and reported in Table 1. All samples were visually opalescent.

Example 4

The suspension stabilization, concentration, and processing conditions are identical as Example 1A except that the brown bodies were sintered in a microwave assisted high temperature furnace, MRF 16/22, Carbolite, Hope Valley, UK.

In Example 4A, the sample was heated at 10° C./min to 1125° C. in IR sensor controlled mode, with microwave on after 700° C. in auto mode. Then the sample dwelled at 1125° C. under 500 W microwave for 2 hours. The sample was cooled down naturally.

In Example 4B, the sample was heated at 10° C./min to 1125° C. in IR sensor controlled mode for 6 s, and then held at 1075° C. for 20 h. During heating, the microwave started at 700° C. in auto mode, and during dwelling the microwave was manually set at 200 W.

Figure 10:
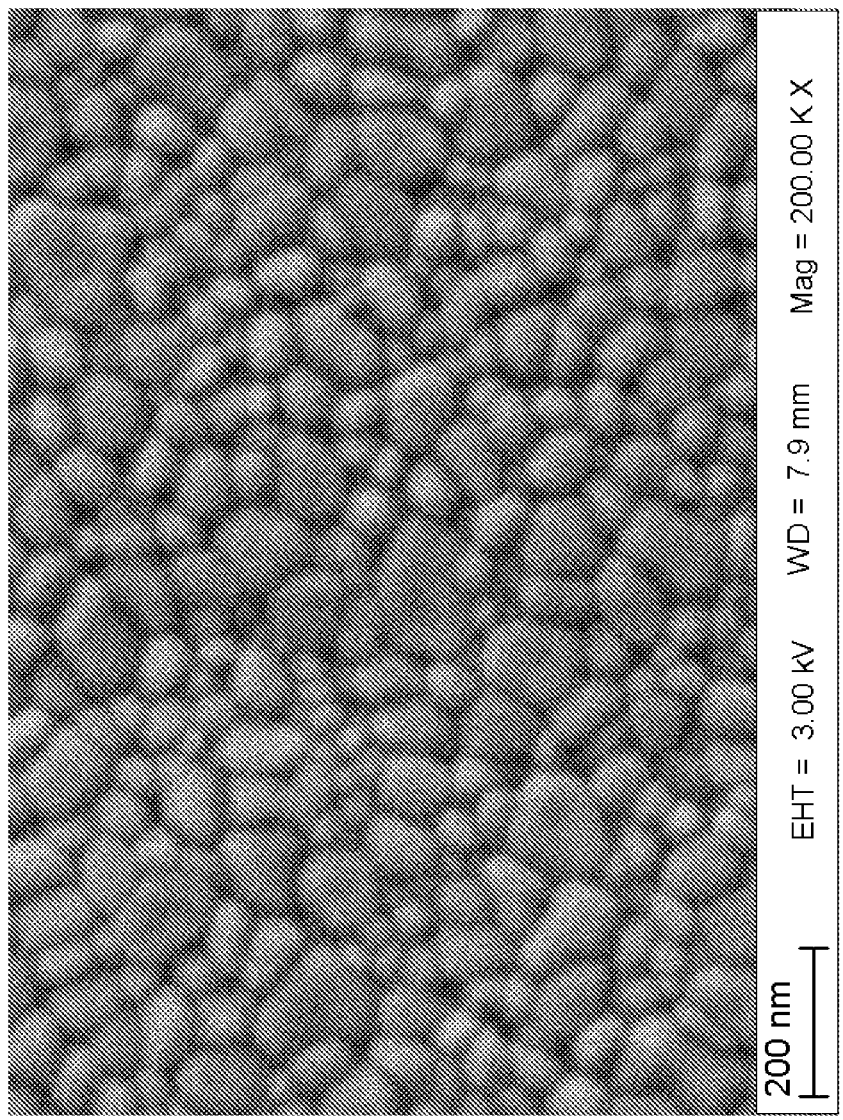
FIG. 10 shows a microstructure of 99.9% dense opalescent nanozirconia body with average grain size of 91 nm sintered in a hybrid microwave furnace in accordance with the present invention as described in Example 4B.
Figure 11A:
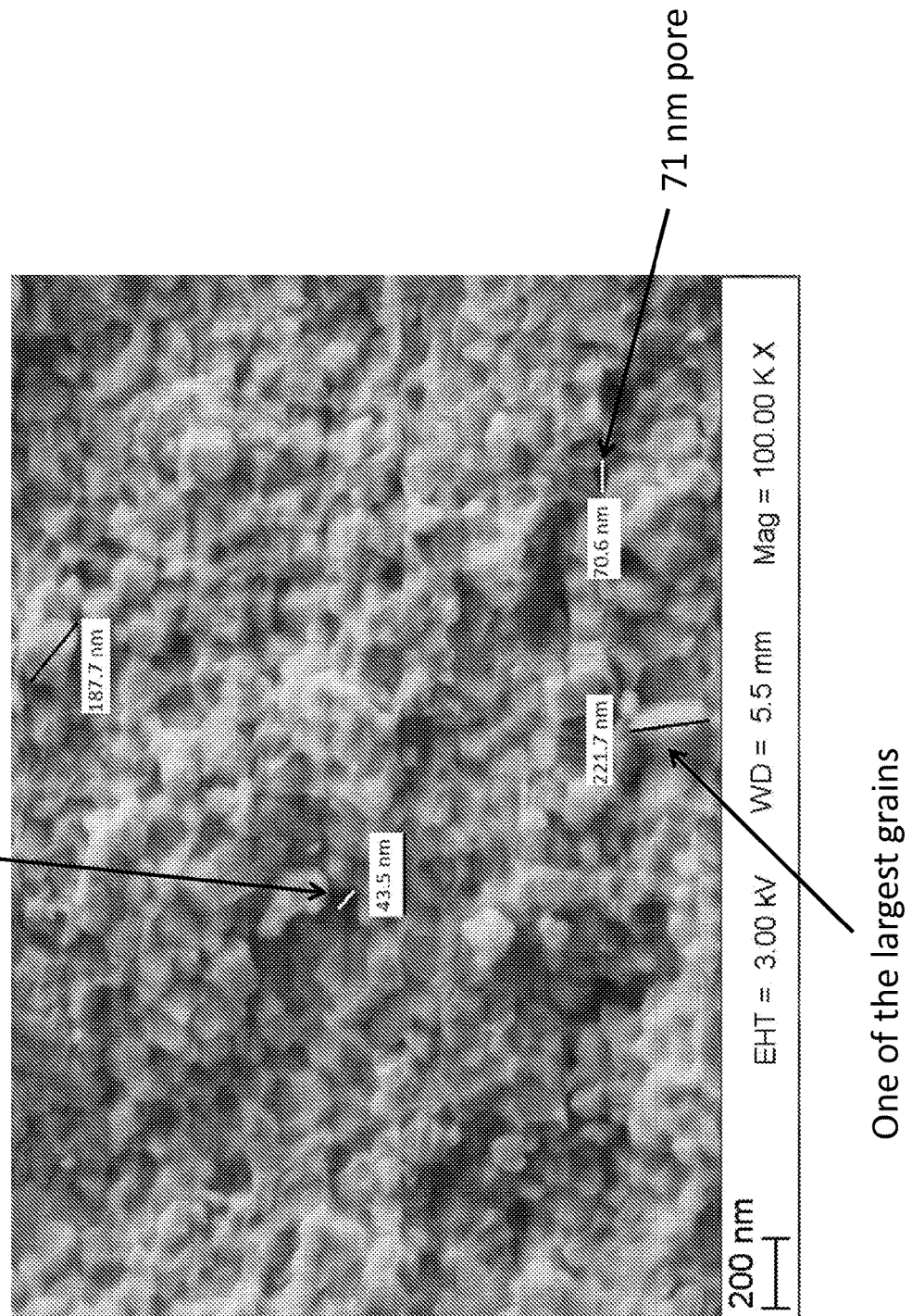
FIGS. 11A, 11B and 11C show fracture surfaces of some of nanozirconia materials of the present invention at various magnifications illustrating typical grain size range and occasional nano-pores with sizes ranging from 30 nm to 100 nm
Figure 11B:
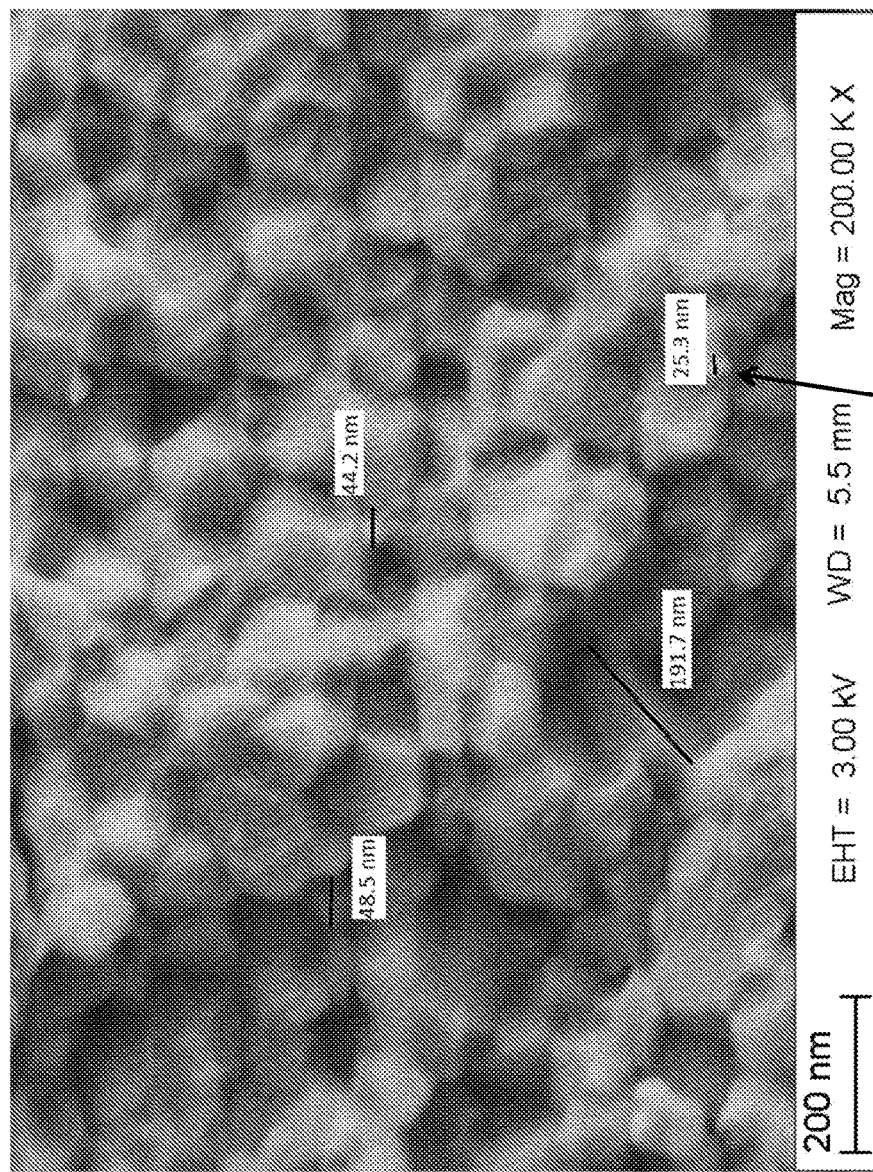
Figure 11C:
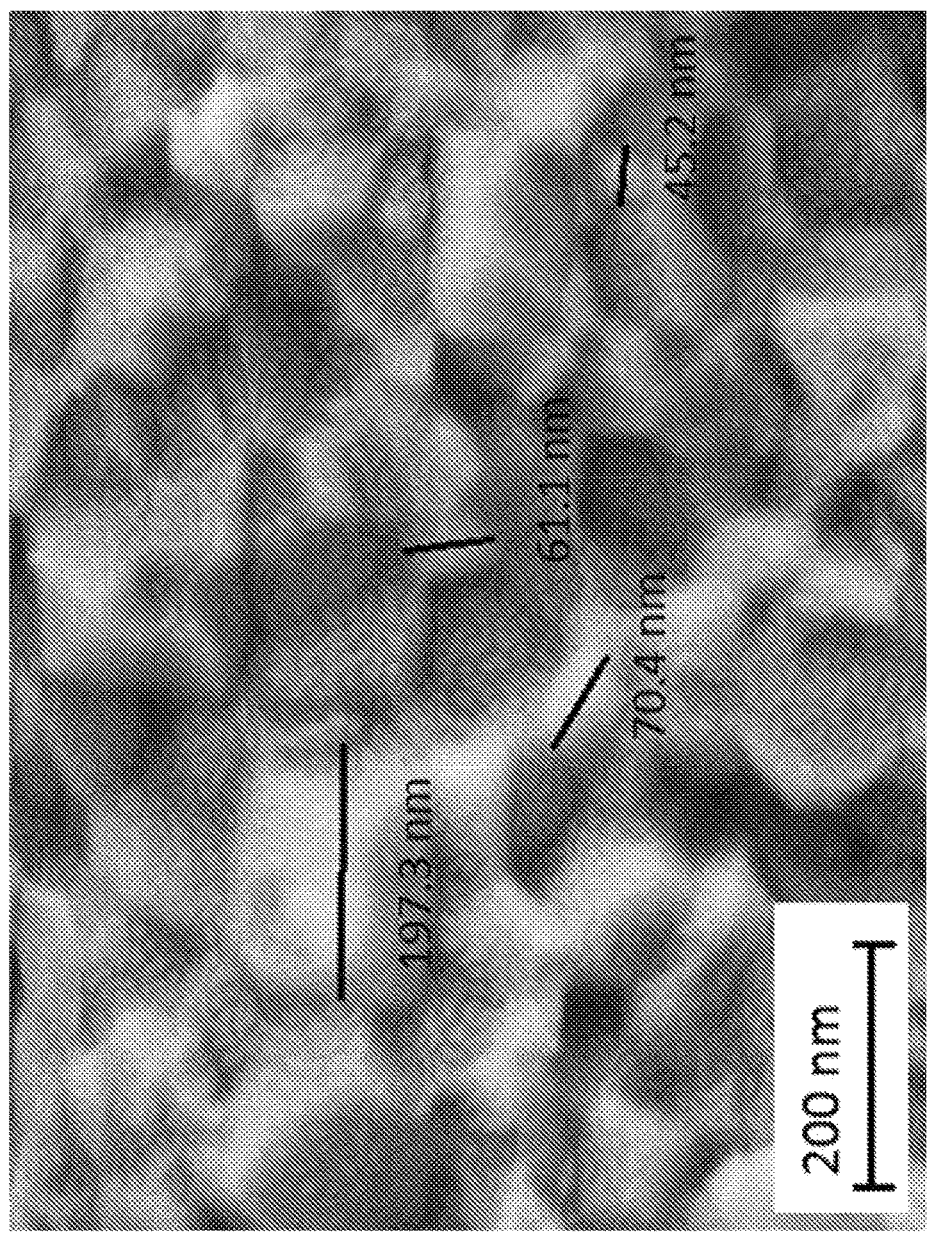
Figure 12:
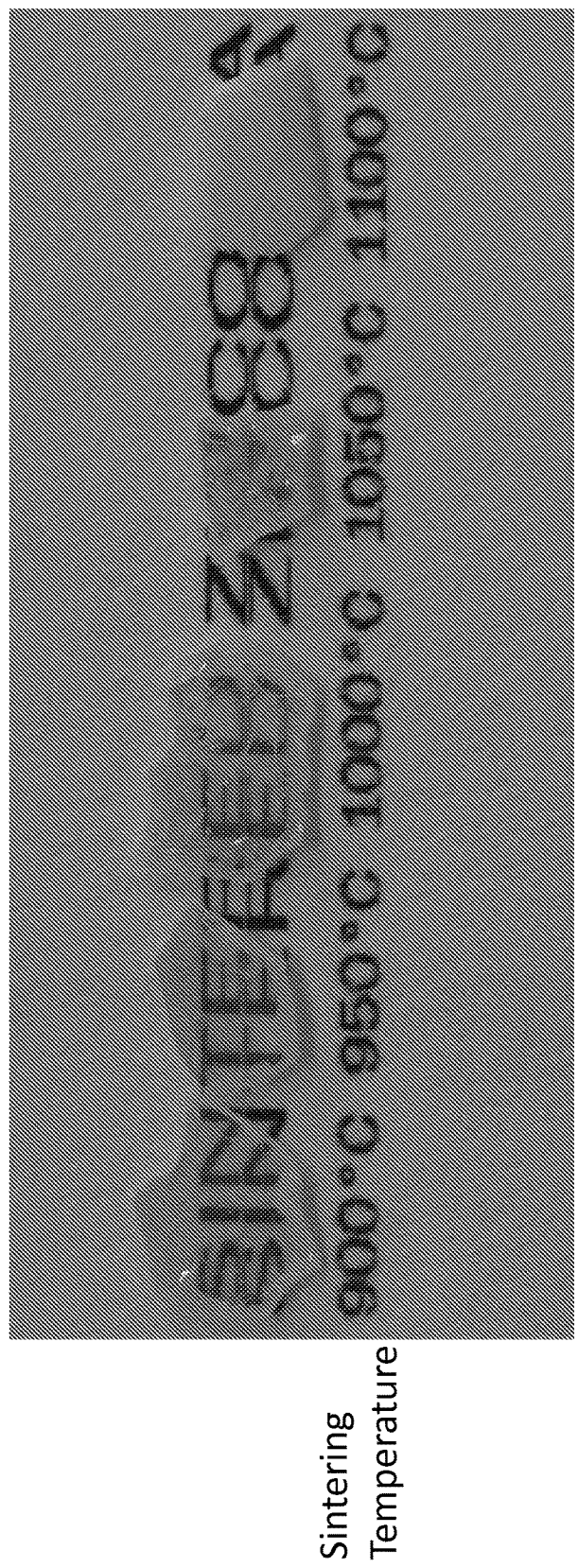
FIG. 12 shows the transition from transparent to opaque nanozirconia bodies made from organic solvent based suspension of $ZrO_2$ nanoparticles without $Y2O3$ or any other tetragonal phase stabilizer.
Figure 13A:
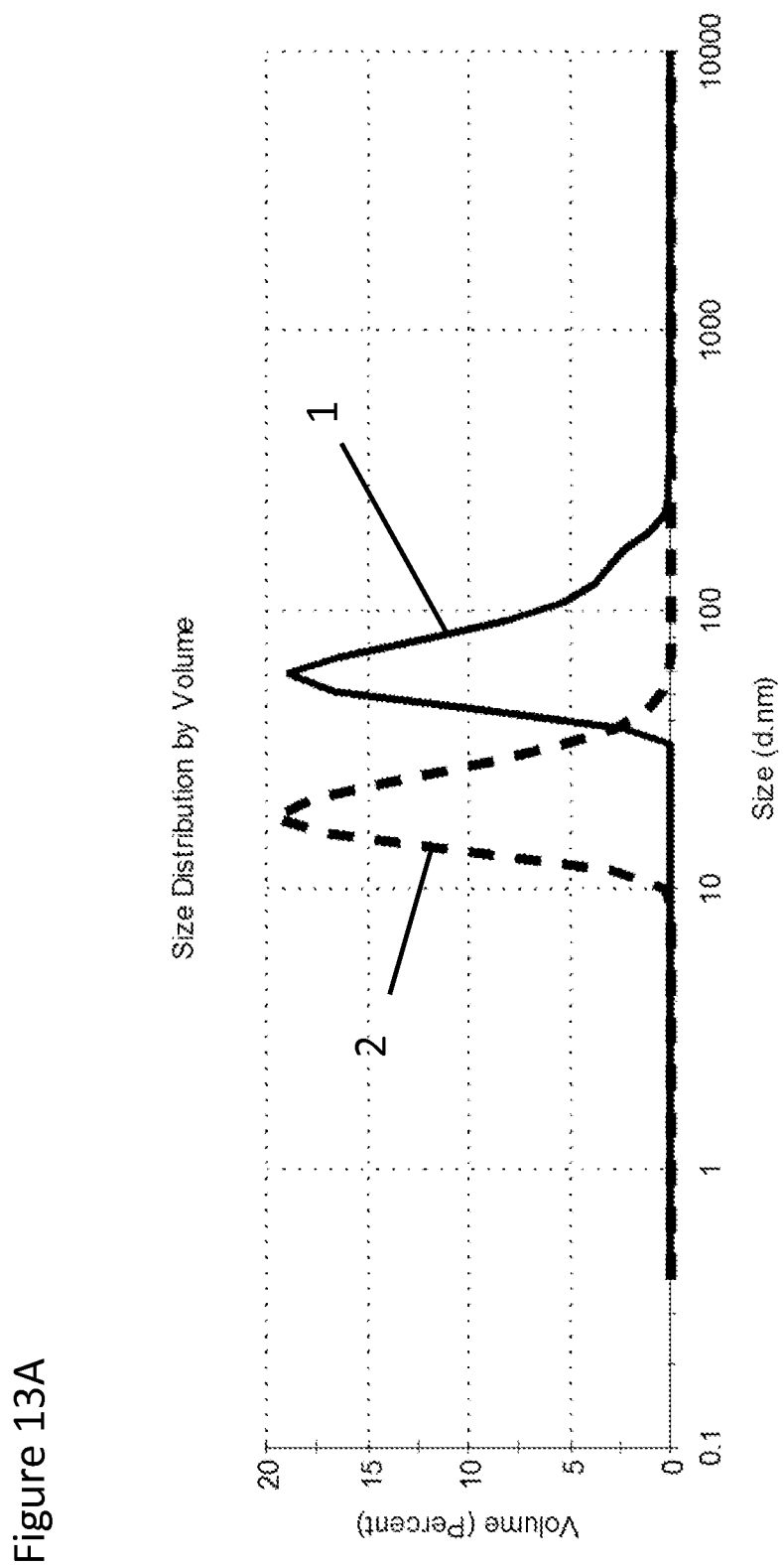
FIG. 13A shows particle size distribution of nanozirconia suspension concentrated to ~17 vol % from 4.5 vol % suspension prior to (1) and after attrition-milling (2).
Figure 13B:
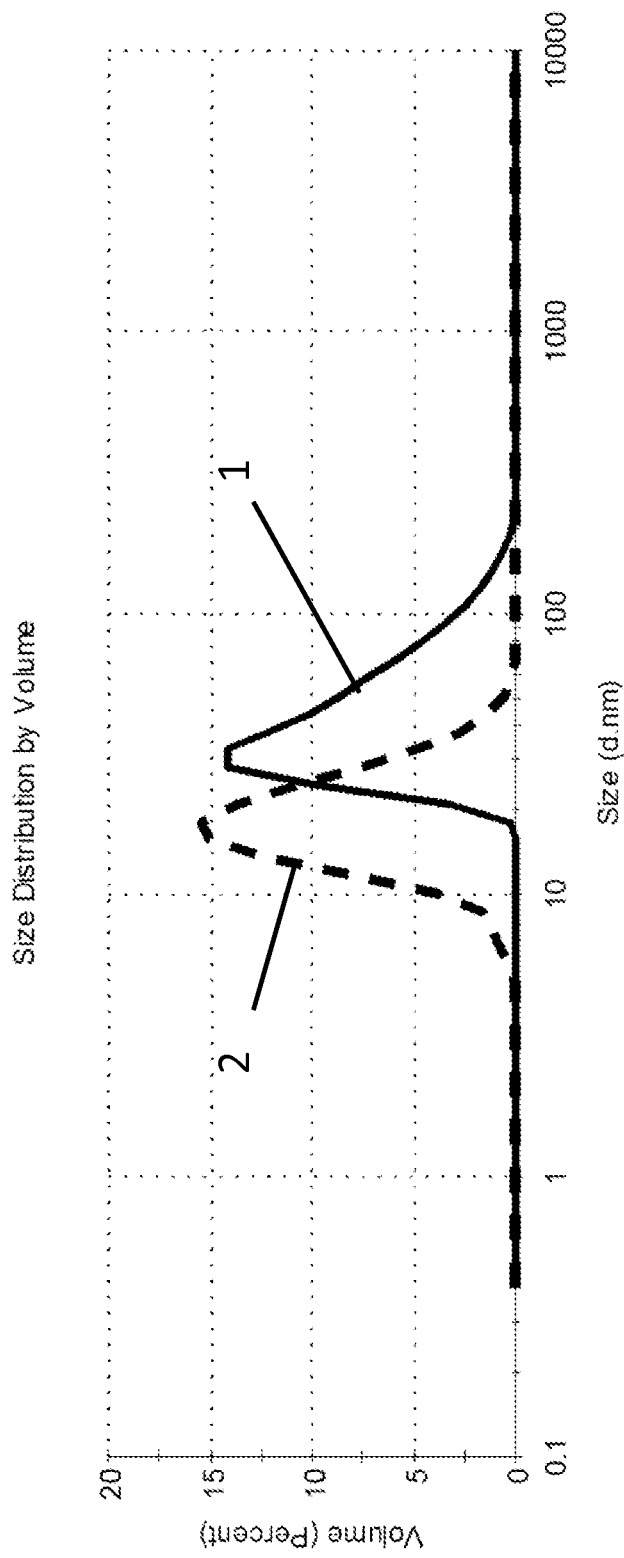
FIG. 13B shows particle size of as-received ~17 vol % nano-zirconia suspension prior to (1) and after attrition-milling (2).

Density and grain size were measured and reported in Table 1. FIG. 10 shows the microstructure of Example 4B with average grain size of 91 nm and density of 99.92%. All such sintered samples are visually opalescent.

Example 5

500 g of 5 vol % aqueous suspension of 3 mol % yttria stabilized zirconia nanoparticulate was received from Mel Chemicals (Flemington, N.J.). This suspension was stabilized by addition of 3 wt % dispersants by weight of solid zirconia. The stabilized suspension was concentrated from 5 vol % to 18 vol % in a glass beaker by heating while stirring at 50° C. for 14 hours in a water bath with a hot plate. Slip casting was carried out using plaster molds, prepared by casting cylinders of 32 mm in diameter, and 30 mm in height with USG No. 1 Pottery Plaster. The cylinders were wrapped with plastic paper for holding the slurries before consolidation. 5 to 15 g of concentrated slurry was poured into each mold depending on the desired final thickness. After the slurry was consolidated, the plastic paper was removed, and the consolidated parts were removed from the plaster and put into a drying box for curing and drying under controlled humidity (identical to Example 1A). After drying, the green bodies were burned out at a rate of 0.5° C./min to 700° C. and held for 2 hours. Brown bodies were sintered in a dental furnace (Programat P500, Ivoclar Vivadent AG.) by heating at a rate of 10° C./min to 1150° C. and held for 2 hours.

The relative density of the so-formed articles was measured to be 99.50%. All such formed articles were visually opalescent.

Example 6

Figure 6:
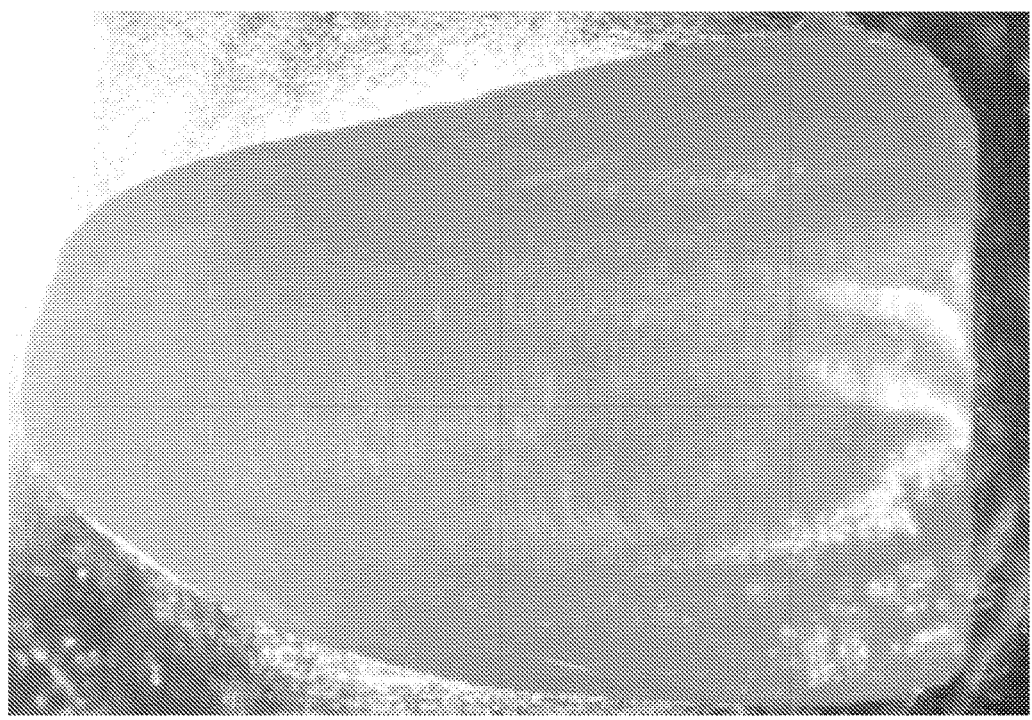
FIG. 6 shows a veneer made from fully dense nanozirconia of the present invention exhibiting clearly visible opalescence.

The suspension was stabilized, concentrated and de-agglomerated in the identical steps as illustrated in Example 1A. 40 ml suspension was then transferred to a PTFE centrifuge vessel and centrifuged at 11000 rpm for 40 min by Legend XT Centrifuge, ThermoScientific. Afterwards, the supernatant was carefully removed by pipetting. The dense bottom part stayed in the PTFE vessel and was subjected to drying for 15 days. After the part was dried completely, it was removed from the mold and burned out at 700° C. for 2 hours. The so-formed brown body was ground into a realistically shaped veneer with an enlargement factor of 1.25 and sintered. Sintering was carried out in Programat P500 dental furnace at 1150° C. for 2 hours, and the density was measured to be 99.90%. The so-formed veneer was polished to a glossy finish with thickness between 0.3-1.5 mm. It appears opalescent as shown in FIG. 6.

Example 7

An organic solvent based nanozirconia suspension (0% $Y_2O_3$) was received from Pixelligent Technologies (Baltimore, Md.). The concentration of as-received suspension was 14.0 vol % with an average particle size of 5 to 8 nm in a toluene solution. This suspension was concentrated by slowly evaporating the solvent under ambient conditions in a PTFE tube. After the part was completely dried, it was then removed from the tube and subjected to burn out at 550° C. for 2 hours. Both green and brown bodies were transparent. Sintering was carried out at temperatures from 900° C. to 1100° C. for 1 hour. The phase and grain size was measured and calculated by grazing incidence X-ray diffraction and SEM, and the results are listed in Table 2. Some opalescence can only be observed in samples sintered at 1000° C. and 1050° C. There is no "tint" observed for any of the sintered bodies; they appeared basically colorless. The highest density for sintered bodies was 98.3%, and all samples showed severe cracking after heat treatment. Results on visual appearance, density, grain size and phase composition are listed in Table 2 below.

TABLE 2

| Sintering temp ° C. | 900 | 950 | 1000 | 1050 | 1100 |
|---|---|---|---|---|---|
| Appearance (see FIG. 12) | "Window" Transparent | "Window" Transparent | Translucent with some opalescence | Translucent with some opalescence | Opaque |
| Density (%) | n/a | 98.3 ± 0.2 | 97.8 ± 0.2 | 95.5 ± 0.1 | NA |
| Grain size estimated from SEM (nm) | na | na | 35 | 40 | 90 |
| Grain Size from XRD (nm) | 7 | 13 | 18 | 22 | 18 |
| Phases | Tetragonal phase | | | | Monoclinic phase >90 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A zirconia dental ceramic comprising:
   predominantly tetragonal zirconia with less than 15% monoclinic and cubic phases combined;
   at least 95% of all grains by volume within the range of 10 nm to 300 nm;
   a density of at least 99.5% of theoretical density; and
   exhibiting opalescence.

2. The zirconia dental ceramic of claim 1, comprising an average grain size from 40 nm to 150 nm.

3. The zirconia dental ceramic of claim 2, comprising an average grain size from 50 nm to 100 nm.

4. The zirconia dental ceramic of claim 3, comprising an average grain size from 50 nm to 80 nm.

5. The zirconia dental ceramic of claim 1, wherein at least 95% of all grains are within the range of 20 nm to 250 nm.

6. The zirconia dental ceramic of claim 1, wherein all the grains are within the range of 10 nm to 300 nm.

7. The zirconia dental ceramic of claim 1, wherein the opalescence is at least 9.

8. The zirconia dental ceramic of claim 7, wherein the opalescence is at least 12 and no greater than 28.

9. The zirconia dental ceramic of claim 1, comprising a visible light transmittance for a one millimeter thickness of greater than 45% at a wavelength in the range of 560 nm to 700 nm.

10. The zirconia dental ceramic of claim 9, comprising a visible light transmittance for a one millimeter thickness of greater than 45% at a wavelength of 560 nm.

11. The zirconia dental ceramic of claim 9, comprising a visible light transmittance for a one millimeter thickness of greater than 50% at a wavelength in the range of 560 nm to 700 nm.

12. The zirconia dental ceramic of claim 11, comprising a visible light transmittance for a one millimeter thickness of greater than 50% at a wavelength of 560 nm.

13. The zirconia dental ceramic of claim 1, comprising a visible light transmittance for a one millimeter thickness of greater than 35% at a wavelength in the range of 560 nm to 700 nm.

14. The zirconia dental ceramic of claim 13, comprising a visible light transmittance for a one millimeter thickness of greater than 35% at a wavelength of 560 nm.

15. The zirconia dental ceramic of claim 13, comprising a visible light transmittance for a one millimeter thickness of greater than 40% at a wavelength in the range of 560 nm to 700 nm.

16. The zirconia dental ceramic of claim 15, comprising a visible light transmittance for a one millimeter thickness of greater than 40% at a wavelength of 560 nm.

17. The zirconia dental ceramic of claim 1, wherein the density is at least 99.9% of theoretical density.

18. The zirconia dental ceramic of claim 1, comprising a flexural strength of at least 800 MPa.

19. The zirconia dental ceramic of claim 18, comprising a flexural strength of at least 1200 MPa.

20. The zirconia dental ceramic of claim 19, comprising a flexural strength of at least 2 GPa.

21. The zirconia dental ceramic of claim 18, comprising a flexural strength of no greater than 2.8 GPa.

22. The zirconia dental ceramic of claim 1, wherein the opalescence is measured on a 1 mm thick sample by using the formula $$OP=[(CIEa_T^*-CIEa_R^*)^2+(CIEb_T^*-CIEb_R^*)^2]^{1/2},$$

wherein $(CIEa_T^*-CIEa_R^*)$ is the difference between transmission and reflectance modes in red-green coordinate a* of CIE L*a*b* color space; and wherein $(CIEb_T^*-CIEb_R^*)$ is the difference between transmission and reflectance modes in yellow-blue color coordinate b* of CIE L*a*b* color space.

23. The zirconia dental ceramic of claim 1, comprising YTZP (yttria-stabilized tetragonal zirconia polycrystal) with 0-3 mol % $Y_2O_3$.

24. The zirconia dental ceramic of claim 1, comprising less than 0.5% porosity, wherein a majority of pores are at least 25 nm in diameter when porosity is greater than 0.1.

25. The zirconia dental ceramic of claim 24, comprising less than 0.5% porosity, wherein a majority of pores are at least 30 nm in diameter when porosity is greater than 0.1.

26. The zirconia dental ceramic of claim 1, wherein the zirconia comprises a stabilizing additive selected from Y, Ce, Mg, or mixtures thereof.

27. A dental article comprising the zirconia dental ceramic of claim 1.

28. The dental article of claim 27, fabricated by shaping a green, brown or pre-sintered zirconia material and sintering it to final density greater than or equal to 99.5% of theoretical density.

29. The dental article of claim 27, formed into blanks, full-contour FPDs (fixed partial dentures), bridges, implant bridges, multi-unit frameworks, abutments, crowns, partial crowns, veneers, inlays, onlays, orthodontic retainers, space maintainers, tooth replacement appliances, splints, dentures, posts, teeth, jackets, facings, facets, implants, cylinders, and connectors.

\* \* \* \* \*